United States Patent
Murata et al.

(10) Patent No.: US 6,372,740 B1
(45) Date of Patent: Apr. 16, 2002

(54) 2-ARYL-8-OXODIHYDROPURINE DERIVATIVE, PROCESS FOR THE PRODUCING THE SAME, MEDICINAL COMPOSITIONS CONTAINING THE SAME, AND INTERMEDIATES THEREOF

(75) Inventors: Teruya Murata, Izumiotsu; Kaoru Masumoto, Neyagawa; Katsunori Kondo, Suita; Kiyoshi Furukawa, Shiga-ken; Makoto Oka, Ibaraki, all of (JP)

(73) Assignee: Dainippon Pharmaceutical Co., Ltd., Osaka-Fu (JP)

( * ) Notice: Subject to any disclaimer, the term of this patent is extended or adjusted under 35 U.S.C. 154(b) by 0 days.

(21) Appl. No.: 09/555,490

(22) PCT Filed: Nov. 26, 1998

(86) PCT No.: PCT/JP98/05320

§ 371 Date: Jun. 1, 2000

§ 102(e) Date: Jun. 1, 2000

(87) PCT Pub. No.: WO99/28320

PCT Pub. Date: Jun. 6, 1999

(30) Foreign Application Priority Data

Dec. 3, 1997 (JP) .............................................. 9-350000

(51) Int. Cl.[7] .................... C02D 473/00; C02D 473/34; A61K 31/522; A61K 31/5377; A61P 25/22

(52) U.S. Cl. .................... 514/234.2; 514/262; 544/118; 544/265; 544/276; 544/322; 544/324

(58) Field of Search ................................. 544/276, 265, 544/118; 514/262, 234.2

(56) References Cited

U.S. PATENT DOCUMENTS

| | | | |
|---|---|---|---|
| 4,499,094 A | 2/1985 | Dubroeucq et al. | 514/301 |
| 4,788,199 A | 11/1988 | Benavides et al. | 514/259 |
| 4,996,213 A | 2/1991 | Mendes et al. | 514/300 |
| 5,026,711 A | 6/1991 | Mendes et al. | 514/300 |
| 5,840,891 A | 11/1998 | Nestor, Jr. et al. | 544/276 |
| 5,856,481 A | 1/1999 | Nestor et al. | 544/276 |
| 5,972,946 A | 10/1999 | Murata et al. | 514/256 |
| 6,028,076 A | 2/2000 | Hirota et al. | 514/262 |
| 6,083,953 A | 7/2000 | Nestor et al. | 514/262 |
| 6,211,195 B1 * | 4/2001 | Webb | 514/301 |

FOREIGN PATENT DOCUMENTS

| | | | |
|---|---|---|---|
| JP | 2-32078 | | 2/1990 |
| JP | 200148882 | * | 2/2001 |
| WO | 98/01448 | | 1/1998 |

OTHER PUBLICATIONS

F. Yoneda et al., "Synthesis of Purines by Cyclization of the Michael–type Adducts from 6–Aminopyrimidines and 4–Phenyl–1,2, 4–triazoline–3, 5–dione", J.C.S. Perkin I, (1977) pp. 2285–2288.

J.L. Kelley et al., "Benzodiazepine Receptor Binding Activity of 9–(1–Phenylethyl) purines", Journal of Medicinal Chemistry, vol. 33, No. 7, (1990), pp. 1910–1914.

E. Romeo et al., "2–Aryl–3–Indoleacetamides (FGIN–1): A New Class of Potent and Specific Ligands for the Mitochondrial DBI Receptor (MDR)", The Journal of Pharmacology and Experimental Therapeutics, vol. 262, No. 3, pp. 971–978, (1992).

F. Yoneda et al., "Synthesis of Purines by Cyclization of the Michael–type Adducts from 6–Aminopyrimidines and 4–Phenyl–1,2,4–triazoline–3,5–dione", J.C.S. Perkin I, pp. 2285–2288, (1977).

J. Kelley et al., "Benzodiazepine Receptor Binding Activity of 9–(1–Phenylethyl)purines", J. Med. Chem., , vol. 33, No. 7, pp. 1910–1914, (1990).

Abstract for HU 216867 (Jul. 1995).

* cited by examiner

*Primary Examiner*—Mark L. Berch
(74) *Attorney, Agent, or Firm*—Wenderoth, Lind & Ponack, L.L.P.

(57) ABSTRACT

2-Aryl-8-oxodihydropurine derivative of the following formula (I):

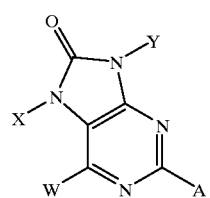

(I)

wherein W is H, lower alkyl, halogen, lower alkoxy, amino, mono- or di-lower alkylamino, or substituted or unsubstituted phenyl; X is H, lower alkyl, cycloalkyl-lower alkyl, substituted or unsubstituted phenyl-lower alkyl, lower alkenyl, carbamoyl, di-lower alkylcarbamoyl, or a group of the formula (Q): —CH(R$^3$)CON(R$^1$)(R$^2$); Y is H, lower alkyl, cycloalkyl, cycloalkyl-lower alkyl, lower alkenyl, substituted or unsubstituted phenyl-lower alkyl, or a group of the formula (Q): —CH(R$^3$)CON(R$^1$)(R$^2$); A is substituted or unsubstituted phenyl, or substituted or unsubstituted heteroaryl; provided that when one of X and Y of the above formula (I) is the group of the formula (Q), then the other is the same groups for X or Y as described above except for the group of the formula (Q), or a pharmaceutically acceptable acid addition salt thereof. These compounds are useful for the prophylaxis or treatment of central nervous disorders such as anxiety-related diseases (neurosis, somatoform disorders, anxiety disorders, and others), depression, epilepsy, etc., or circulatory organs disorders such as angina pectoris, hypertension.

18 Claims, No Drawings

2-ARYL-8-OXODIHYDROPURINE DERIVATIVE, PROCESS FOR THE PRODUCING THE SAME, MEDICINAL COMPOSITIONS CONTAINING THE SAME, AND INTERMEDIATES THEREOF

This application is a 371 of PCT/JP98/05320 filed Nov. 26, 1998.

TECHNICAL FIELD

The present invention relates to a novel 2-aryl-8-oxodihydro-purine derivative selectively acting on the peripheral-type benzo-diazepine receptors, more particularly, a 2-aryl-8-oxodihydropurine derivative having an acetamide moiety at the 7-position or the 9-position of the purine nucleus, a process for the preparation thereof, a pharmaceutical composition containing the same, and an intermediate therefor.

BACKGROUND ART

In the tissues of the mammals including human, there are three kinds of benzodiazepine (hereinafter, occasionally referred to as BZ) recognition sites, and each is named as central-type ($\omega_1, \omega_2$) benzodiazepine receptors and a peripheral-type ($\omega_3$) benzodiazepine receptor, respectively (hereinafter, occasionally referred to as $BZ\omega_1$-receptor, $BZ\omega_2$-receptor and $BZ\omega_3$-receptor, respectively). Among them, the central-type BZ-receptors are the binding sites for BZ-compounds, and are present on the γ-aminobutyric acid (hereinafter, occasionally referred to as "GABA")$_A$-BZ-receptor-Cl$^-$ ion channel complexes. On the other hand, the peripheral-type BZ-receptor widely distributes in the central or peripheral tissues or organs such as brain, kidney, liver, heart, etc., and it especially distributes with high density in the cells of the endocrinium organs such as adrenal glands, testicles, etc., or in the cells deeply participating in the inflammation-immune system in whole body such as mast cells, lymphocytes, macrophages, blood platelets, etc., so that the physiological roles of the peripheral-type BZ-receptor have recently been drawing attention. On the other hand, the peripheral-type BZ-receptor is present a lot in the mitochondrial membrane of glial cells in the brain, and it participates in cholesterol influx into the mitochondrial membrane, and hence, it is thought to act on the biosynthesis pathway of cholesterol into neurosteroids such as progesterone, allopregnanolone, etc., via pregnenolone. Thus, it is considered that stimulation of the peripheral-type BZ-receptor accelerates the synthesis of neurosteroids in the brain which affect the chloride ion channel gating process by binding to the neurosteroid-specific recognition site (which is a different site from the benzodiazepine receptor) on the GABA$_A$-BZ receptor-Cl$^-$ ion channel complexes [cf. Romeo, E., et al., J. Pharmacol. Exp. Ther., 262, 971–978 (1992)].

A compound having a non-BZ nucleus and selectively showing an affinity for the peripheral-type BZ-receptor has been disclosed in Japanese Patent First Publication (Kokai) No. 201756/1983 (=EP-A-94271), and since then, various compounds have been disclosed in many patent publications, etc., however, there is no compound which has actually been used as a medicament.

As a compound having a non-BZ nucleus and selectively showing an affinity for the peripheral-type BZ-receptors, the following compounds have been known.

Japanese Patent First Publication (Kokai) No. 5946/1987 (=U.S. Pat. No. 4,788,199, EP-A-205375 (patent family)) discloses that amide compounds of the following formula are bound to the peripheral-type BZ-receptor, and are useful as anxiolytics, anticonvulsants and drugs for treatment of angina pectoris, and in the treatment of immuno-deficiency syndrome.

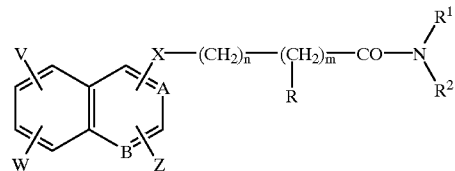

Japanese Patent First Publication (Kokai) No. 32058/1990 (=EP-A-346208, U.S. Pat. No. 5,026,711) discloses that 4-amino-3-carboxyquinoline compounds of the following formula show an affinity for the peripheral-type BZ-receptor both in vitro and in vivo, and can be used in the prophylaxis or treatment of human cardiovascular diseases, or as an antiallergic agent, or in the prophylaxis or treatment of infectious diseases, or in the treatment of anxiety.

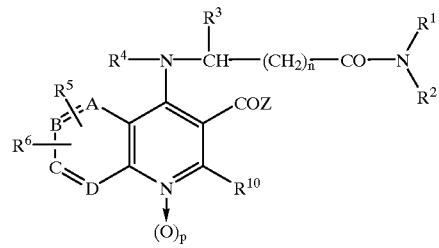

WO 96-32383 publication discloses that the acetamide derivative of the following formula selectively acts on $BZ\omega_3$-receptor, and has anxiolytic activity and anti-rheumatoid activity so that it can be used in the treatment of anxiety-relating diseases or immune diseases.

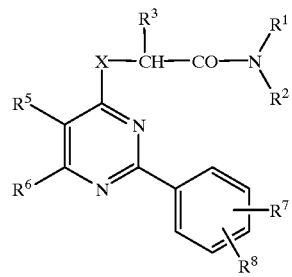

wherein X is —O— or —NR$^4$—; R$^1$ is a hydrogen atom, a lower alkyl group, a lower alkenyl group, or a cycloalkyl-lower alkyl group; R$^2$ is a lower alkyl group, a cycloalkyl group, a substituted or unsubstituted phenyl group, a substituted or unsubstituted phenyl-lower alkyl group, etc.; R$^3$ is a hydrogen atom, a lower alkyl group, or a hydroxy-lower alkyl group; R$^4$ is a hydrogen atom, a lower alkyl group, etc.; R$^5$ is a hydrogen atom, a lower alkyl group, a lower alkenyl group, a hydroxy-lower alkyl group, a substituted or unsubstituted benzyloxy-lower alkyl group, an acyloxy-lower alkyl group, a lower alkoxy-lower alkyl group, an amino group, a mono- or di-lower alkylamino group, an acylamino group, an amino-lower alkyl group, a nitro group, a carbamoyl group, a mono- or di-lower alkylcarbamoyl group, a carboxyl group, a protected carboxyl group, a carboxy-lower alkyl group, or a protected carboxy-lower alkyl group; $R^6$ is a hydrogen atom, a lower alkyl group, a trifluoromethyl group, or a substituted or unsubstituted phenyl group, or $R^5$ and $R^6$ may optionally combine to form —$(CH_2)_n$— (n is 3, 4, 5 or 6); $R^7$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group; and $R^8$ is a hydrogen atom, a halogen atom, a lower alkyl group, or a lower alkoxy group.

DISCLOSURE OF INVENTION

The present inventors have intensively studied in order to prepare a compound acting selectively and potently on $BZ\omega_3$-receptor, and have found the 2-aryl-8-oxodihydropurine derivatives of the following formula (I), and finally have accomplished the present invention.

An object of the present invention is to provide a novel 2-aryl-8-oxodihydropurine derivative acting selectively and potently on $BZ\omega_3$-receptor, more particularly, to provide a 2-aryl-8-oxodihydropurine derivative having an acetamide moiety on the 7-position or the 9-position of the purine nucleus. Especially, the present invention provides a useful compound having an anti-anxiety activity. Another object of the present invention is to provide a process for preparing said compound. Still further object of the present invention is to provide a pharmaceutical composition containing said compound. Further object of the present invention is to provide an intermediate for preparing said compound. These and other objects and advantages of the present invention are obvious to any person skilled in the art from the following disclosure.

The present invention provides a 2-aryl-8-oxodihydropurine derivative of the following formula (I), a pharmaceutically acceptable acid addition salt thereof, a process for the same, and a pharmaceutical composition containing the same:

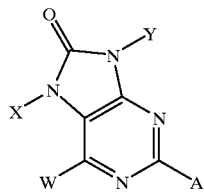

(I)

wherein
W is a hydrogen atom, a lower alkyl group, a halogen atom, a lower alkoxy group, an amino group, a mono- or di-lower alkylamino group, or a substituted or unsubstituted phenyl group;
X is a hydrogen atom, a lower alkyl group, a cycloalkyl-lower alkyl group, a substituted or unsubstituted phenyl-lower alkyl group, a lower alkenyl group, a carbamoyl group, a di-lower alkylcarbamoyl group, or a group of the formula (Q):

—CH($R^3$)CON($R^1$)($R^2$)     (Q)

(wherein $R^1$ is a lower alkyl group, a lower alkenyl group, a cycloalkyl group, a cycloalkyl-lower alkyl group, or a hydroxy-lower alkyl group, $R^2$ is a lower alkyl group, a cycloalkyl group, a substituted or unsubstituted phenyl group, a substituted or unsubstituted phenyl-lower alkyl group, or a substituted or unsubstituted heteroaryl group, or $R^1$ and $R^2$ may combine together with the adjacent nitrogen atom to form a piperidine ring, a pyrrolidine ring, a morpholine ring, or a piperazine ring, and these rings may optionally be substituted by one or two lower alkyl groups, and $R^3$ is a hydrogen atom, a lower alkyl group, or a hydroxy-lower alkyl group);
Y is a hydrogen atom, a lower alkyl group, a cycloalkyl group, a cycloalkyl-lower alkyl group, a lower alkenyl group, a substituted or unsubstituted phenyl-lower alkyl group, or a group of the formula (Q):

—CH($R^3$)CON($R^1$)($R^2$)     (Q)

(wherein $R^1$, $R^2$ and $R^3$ are the same as defined above); and
A is a substituted or unsubstituted phenyl group, or a substituted or unsubstituted heteroaryl group;
provided that when one of X and Y of the above formula (I) is the group of the formula (Q), then the other is the same groups as defined for X or Y except for the group of the formula (Q), and also provides an intermediate of the following formula (II):

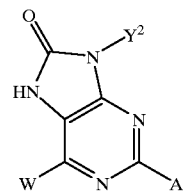

(II)

wherein
$Y^2$ is a hydrogen atom, a lower alkyl group, a cycloalkyl group, a cycloalkyl-lower alkyl group, a lower alkenyl group, or a substituted or unsubstituted phenyl-lower alkyl group; and
A and W are the same as those as defined above.

The pharmaceutically acceptable acid addition salt of the compound of the formula (I) includes a pharmaceutically acceptable acid addition salt of the compound of the formula (I) which shows basicity enough to form an acid addition salt thereof, for example, a salt with an inorganic acid such as hydrochloride, hydrobromide, hydroiodide, sulfate, phosphate, etc., or a salt with an organic acid such as maleate, fumarate, oxalate, citrate, tartrate, lactate, benzoate, methanesulfonate, etc.

The compound of the formula (I) and the intermediate thereof, i.e., the compound of the formula (II), and their acid addition acid salts may exist in the form of a hydrate and/or a solvate, and the present invention also includes these hydrates and solvates as well.

The compound of the formula (I) may have one or more asymmetric carbon atoms, and by which stereoisomers thereof are possible, and the compound of the formula (I) may exist in a mixture of two or more stereoisomers. The present invention also includes these stereoisomers, a mixture thereof, and a racemic mixture thereof.

The positions of the purine nucleus of the 2-aryl-8-oxodihydropurine derivative of the present invention are numbered as shown in the following formula, and the compounds disclosed in the present specification are named according to these numbers.

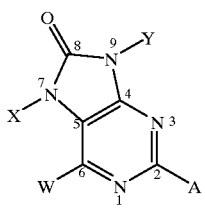

(I)

wherein

A, W, X and Y are the same as defined above.

The terms used in the present description and claims are explained below.

The lower alkyl group and the lower alkyl moiety include a straight chain or branched chain alkyl group having 1 to 6 carbon atoms, unless defined otherwise. The "lower alkyl group" is, for example, methyl, ethyl, propyl, isopropyl, butyl, isobutyl, pentyl, and hexyl, but the preferable lower alkyl group is one having 1 to 4 carbon atoms. The "lower alkoxy group" includes an alkoxy group having 1 to 6 carbon atoms, for example, methoxy, ethoxy, propoxy, isopropoxy, butoxy, etc. The "lower alkenyl group" includes ones having a double bond at any position except for between the 1- and 2-positions, and having 3 to 6 carbon atoms, for example, allyl, and 2-butenyl. The "cycloalkyl group" includes ones having 3 to 8 carbon atoms, for example, cyclopropyl, cyclobutyl, cyclopentyl, cyclohexyl, cycloheptyl, and cyclooctyl. The "cycloalkyl-lower alkyl group" includes an alkyl group having 1 to 4 carbon atoms which is substituted by one of the above mentioned "cycloalkyl groups", for example, cyclopropylmethyl, cyclopentylmethyl, and cyclohexylmethyl. The "hydroxy-lower alkyl group" includes a lower alkyl group being substituted by a hydroxy group, for example, hydroxymethyl, 2-hydroxyethyl, and 3-hydroxypropyl. The "halogen atom" is fluorine, chlorine, bromine, and iodine. The "mono- or di-lower alkylamino group" includes an amino group being substituted by one or two alkyl groups having 1 to 4 carbon atoms, for example, methylamino, ethylamino, propylamino, dimethylamino, diethylamino, dipropylamino, and ethylmethylamino.

The "substituted or unsubstituted phenyl group" includes a phenyl group which may optionally be substituted by one or two groups selected from the group consisting of a halogen atom, a lower alkyl group, a lower alkoxy group, a trifluoromethyl group, a hydroxy group, an amino group, a mono- or di-lower alkylamino group, a cyano group and a nitro group, for example, phenyl; 2-, 3- or 4-chlorophenyl; 2-, 3- or 4-bromophenyl; 2-, 3- or 4-fluorophenyl; 2,4-dichlorophenyl; 2,4-dibromophenyl; 2,4-difluorophenyl; 2-, 3- or 4-methylphenyl; 2-, 3- or 4-methoxyphenyl; 2-, 3- or 4-trifluoromethylphenyl; 2-, 3- or 4-hydroxyphenyl; 2-, 3- or 4-aminophenyl; 2-, 3- or 4-methylaminophenyl; 2-, 3- or 4-dimethylaminophenyl; 2-, 3- or 4-cyanophenyl; and 2-, 3- or 4-nitrophenyl.

The "substituted or unsubstituted phenyl-lower alkyl group" includes an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxy group, an amino group, a mono- or di-lower alkylamino group, a cyano group and a nitro group, for example, benzyl; 2-, 3- or 4-chlorobenzyl; 2-, 3- or 4-bromobenzyl; 2-, 3- or 4-fluorobenzyl; 2,4-dichlorobenzyl; 2,4-dibromobenzyl; 2,4-difluorobenzyl; 2-, 3- or 4-methylbenzyl; 2-, 3- or 4-methoxybenzyl; 2-, 3- or 4-trifluoromethylbenzyl; 2-, 3- or 4-hydroxybenzyl; 2-, 3- or 4-aminobenzyl; 2-, 3- or 4-methylaminobenzyl; 2-, 3- or 4-dimethylaminobenzyl; 2-, 3- or 4-cyanobenzyl; 2-, 3- or 4-nitrobenzyl; phenethyl; and 2-(4-chlorophenyl)ethyl.

The examples of a group of the formula (A") as described below:

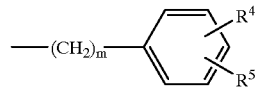

(A")

include the above-mentioned "substituted or unsubstituted phenyl group" or an alkyl group having 1 to 2 carbon atoms which is substituted by the above-mentioned "substituted or unsubstituted phenyl group", and more preferable ones are phenyl, 4- or 3-chlorophenyl, 4- or 3-bromophenyl, 4- or 3-fluorophenyl, 4-methoxyphenyl, 4-tirfluoromethylphenyl, 4-hydroxyphenyl, benzyl, 2-, 3- or 4-chlorobenzyl, 4-bromobenzyl, 3- or 4-fluorobenzyl, 4-methylbenzyl, 4-methoxybenzyl, 4-trifluoromethylbenzyl, 4-hydroxybenzyl, phenethyl, and 2-(4-chlorophenyl)ethyl.

The "substituted or unsubstituted heteroaryl group" includes a 5-membered or 6-membered monocyclic heteroaryl group or a 5-membered or 6-membered bicyclic heteroaryl group, which may optionally be substituted by a $C_1$–$C_3$ alkyl group or a trifluoromethyl group, and has at least one of a nitrogen atom, an oxygen atom and a sulfur atom, for example, 2-, 3- or 4-pyridyl, 5-methyl-2-pyridyl, 2- or 3-thienyl, 2- or 3-furyl, 2-, 4- or 5-pyrimidinyl, 2- or 3-pyrazinyl, 1-pyrazolyl, 2-imidazolyl, 2-thiazolyl, 2-isoxazolyl, 5-methyl-3-isoxazolyl, quinolyl, and isoquinolyl.

Among the compounds of the present invention, the preferable one is a compound of the formula (I) wherein A is a group of the formula (A'):

(A')

(wherein $R^4$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group, and $R^5$ is a hydrogen atom, a halogen atom, a lower alkyl group, a lower alkoxy group, or a hydroxy group), a pyridyl group, a thienyl group, or a furyl group, and W, X and Y are the same as defined above, or a pharmaceutically acceptable acid addition salt thereof.

The more preferable compounds are compounds of the formula (I) wherein (a)

X is a group of the formula (Qx):

—CH($R^{31}$)CON($R^{11}$)($R^{21}$)      (Qx)

wherein $R^{11}$ is a lower alkyl group, and $R^{21}$ is a lower alkyl group or a group of the formula (A"):

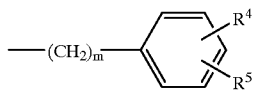

(wherein $R^4$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group, $R^5$ is a hydrogen atom, a halogen atom, a lower alkyl group, a lower alkoxy group, or a hydroxy group, and m is 0, 1 or 2), or $R^{11}$ and $R^{21}$ may combine together with the adjacent nitrogen atom to form a piperidine ring, a pyrrolidine ring, a morpholine ring, or a piperazine ring, and these rings may optionally be substituted by one or two lower alkyl groups, and $R^{31}$ is a hydrogen atom, a lower alkyl group, or a hydroxy-lower alkyl group, and Y is a hydrogen atom or a lower alkyl group, or (b)

X is a hydrogen atom, a lower alkyl group, or a carbamoyl group, and

Y is a group of the formula (Qy):

wherein $R^{11}$, $R^{21}$, and $R^{31}$ are the same as defined above, A is the group of the above formula (A'), a pyridyl group, a thienyl group, or a furyl group, and W is the same as defined above, or a pharmaceutically acceptable acid addition salt thereof.

The further preferable compounds are compounds of the formula (I) wherein (a)

X is the group of the above formula (Qx) (wherein $R^{11}$ is a methyl group, an ethyl group, a propyl group, an isopropyl group, or a butyl group, $R^{21}$ is an ethyl group, a propyl group, an isopropyl group, a butyl group, a phenyl group, a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is the same as defined above), and Y is a hydrogen atom, a methyl group, or an ethyl group, or (b)

X is a hydrogen atom, a methyl group, an ethyl group, a propyl group, an isopropyl group, or a butyl group, and Y is the group of the above formula (Qy) (wherein $R^{11}$ is a methyl group, an ethyl group, a propyl group, an isopropyl group, or a butyl group, $R^{21}$ is an ethyl group, a propyl group, an isopropyl group, a butyl group, a phenyl group, a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is the same as defined above), A is a group of the above formula (A'), a pyridyl group, a thienyl group, or a furyl group, and W is the same as defined above, or a pharmaceutically acceptable acid addition salt thereof.

The especially preferable compounds are 2-aryl-8-oxodihydropurine derivatives of the following formula (Ia) or (Ib), or a pharmaceutically acceptable acid addition salt thereof.

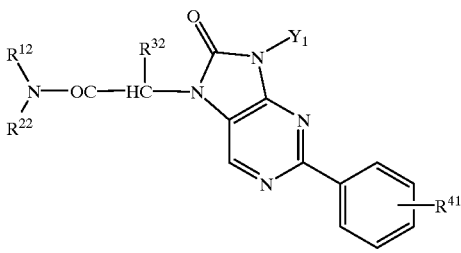

wherein $R^{12}$ and $R^{22}$ are the same or different, and each an ethyl group, a propyl group or a butyl group, or $R^{12}$ is a methyl group, an ethyl group, or a propyl group, $R^{22}$ is a phenyl group, a halogenophenyl group, a methoxyphenyl group, a benzyl group, a halogenobenzyl group, or a methoxybenzyl group, $R^{32}$ is a hydrogen atom, a methyl group, or an ethyl group, $Y^1$ is a hydrogen atom, a methyl group, or an ethyl group, $R^{41}$ is a hydrogen atom, a halogen atom, a methyl group, a methoxy group, a nitro group, or a trifluoromethyl group.

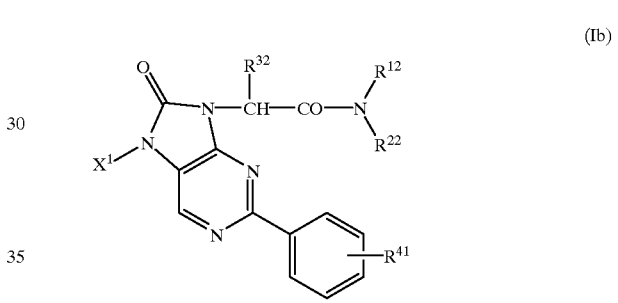

wherein $X^1$ is a hydrogen atom, a methyl group, an ethyl group, or a propyl group, $R^{12}$ and $R^{22}$ are the same or different, and each an ethyl group, a propyl group, or a butyl group, or $R^{12}$ is a methyl group, an ethyl group, or a propyl group, and $R^{22}$ is a phenyl group, a halogenophenyl group, a methoxyphenyl group, a benzyl group, a halogenobenzyl group, or a methoxybenzyl group, $R^{32}$ is a hydrogen atom, a methyl group, or an ethyl group, and $R^{41}$ is a hydrogen atom, a halogen atom, a methyl group, a methoxy group, a nitro group, or a trifluoromethyl group.

The compounds of the formula (Ia) or (Ib) wherein $R^{32}$ is a hydrogen atom are more preferable.

The examples of the most preferable compound of the present invention are the following compounds, and pharmaceutically acceptable acid addition salts thereof.

N-ethyl-8,9-dihydro-9-methyl-8-oxo-2-phenyl-N-phenyl-7H-purin-7-acetamide;

8,9-dihydro-9-methyl-N-methyl-8-oxo-2-phenyl-N-phenyl-7H-purin-7-acetamide;

8,9-dihydro-2-(4-fluorophenyl)-9-methyl-N-methyl-8-oxo-N-phenyl-7H-purin-7-acetamide;

N-ethyl-8,9-dihydro-2-(4-fluorophenyl)-9-methyl-8-oxo-N-phenyl-7H-purin-7-acetamide;

7,8-dihydro-7-methyl-8-oxo-2-phenyl-N,N-dipropyl-9H-purin-9-acetamide;

7-ethyl-7,8-dihydro-8-oxo-2-phenyl-N,N-dipropyl-9H-purin-9-acetamide;

N-benzyl-N-ethyl-7,8-dihydro-7-methyl-8-oxo-2-phenyl-9H-purin-9-acetamide;

N-benzyl-7,8-dihydro-N-methyl-7-methyl-8-oxo-2-phenyl-9H-purin-9-acetamide;
N-benzyl-N-ethyl-7,8-dihydro-7-methyl-8-oxo-2-(4-chlorophenyl)-9H-purin-9-acetamide;
N-benzyl-7,8-dihydro-N-methyl-7-methyl-8-oxo-2-(4-chlorophenyl)-9H-purin-9-acetamide;

The representative compounds of the present invention are, in addition to the compounds of the following Examples, the compounds of the following formulae as listed in Tables 1 and 2, and a pharmaceutically acceptable acid addition salt thereof.

In Tables 1 and 2, the following Reference Examples and Examples, the following abbreviations are used in order to simplify the disclosure.

| | |
|---|---|
| Me: | Methyl group |
| Et: | Ethyl group |
| Pr: | n-Propyl group |
| Bu: | n-Butyl group |
| Pent: | n-Pentyl group |
| (cyclopropyl structure): | Cyclopropyl group |
| —CH$_2$—(cyclopropyl): | Cyclopropylmethyl group |
| Bzl: | Benzyl group |
| Ph: | Phenyl group |
| Py: | Pyridyl group |
| Fur: | Furyl group |
| Thi: | Thienyl group |

Thus, for example, Ph-4-Cl means 4-chlorophenyl group, and Ph-4-F means 4-fluorophenyl group, and 2-Thi means 2-thienyl group.

TABLE 1

[Chemical structure showing purine derivative with substituents R$^1$, R$^2$, R$^3$, A, Y, W]

| R$^1$ | R$^2$ | R$^3$ | A | Y | W |
|---|---|---|---|---|---|
| Et | Pr | H | Ph | Et | H |
| Et | Pr | —CH$_2$OH | Ph | Me | H |
| Pr | Pr | H | Ph | Me | Me |
| Pr | Pr | H | Ph-3-F | Me | H |
| Pr | Pr | Me | Ph | Me | H |
| Pr | Pr | H | 4-Py | Me | H |
| Pr | Pr | H | 2-Fur | Me | Me |
| Pr | Pr | H | Ph-3-Cl | Me | Me |
| Me | Ph | H | Ph-3-F | Me | H |
| Me | Ph | Me | Ph | Me | H |
| Me | Ph | —CH$_2$OH | Ph | Me | H |
| Me | Ph | H | Ph | Me | Me |
| Me | Ph | H | 4-Py | Me | H |
| Me | Ph | H | 3-Thi | Me | H |
| Me | Ph-3-F | H | Ph | Me | H |
| Me | Ph-4-Cl | H | Ph | Me | H |
| Me | —CH$_2$Ph | H | 3-Py | Me | H |
| Me | —CH$_2$Ph | H | Ph | Me | Me |
| Me | —CH$_2$CH$_2$Ph | H | Ph | Me | H |
| —CH$_2$CH=CH$_2$ | —CH$_2$Ph | H | Ph | Me | H |
| Et | Ph | H | Ph | cyclopropyl | H |
| Et | Ph | H | Ph | —CH$_2$-cyclopropyl | H |
| Et | Ph | H | Ph-4-F | —CH$_2$CH=CH$_2$ | H |
| Et | Ph | —CH$_2$OH | Ph | Me | H |
| Et | Ph | H | Ph-2-F | Me | Me |
| Et | Ph | H | Ph-3-F | Me | H |
| Et | Ph | H | Ph-4-F | Me | Me |
| Et | Ph | H | 4-Py | Me | H |
| Et | Ph-2-F | H | Ph | Me | Me |
| Et | Ph-3-F | H | Ph | Me | H |
| Et | Ph-4-OMe | H | Ph-4-F | Me | H |

TABLE 1-continued

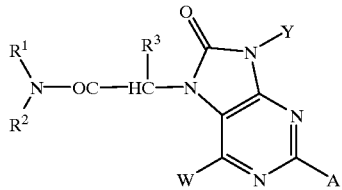

| R¹ | R² | R³ | A | Y | W |
|---|---|---|---|---|---|
| Et | Ph | H | Ph | Me | Me |
| Et | Ph | H | Ph-2-Cl | Me | H |
| Et |  | H | Ph | Me | H |

TABLE 2

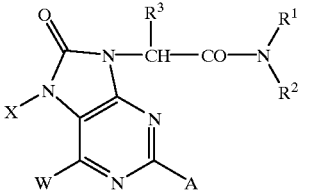

| R¹ | R² | R³ | A | X | W |
|---|---|---|---|---|---|
| Et | Pr | H | Ph | —CONH$_2$ | H |
| Et | Pr | H | Ph-4-F | Me | H |
| Pr | Pr | Me | Ph | Me | H |
| Pr | Pr | H | Ph-4-F | Me | Me |
| Pr | Pr | H | Ph-3-F | 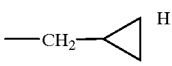 | H |
| Pr | Pr | H | Ph | —CH$_2$CH=CH$_2$ | Me |
| Pr | Pr | —CH$_2$OH | Ph | H | H |
| Pr | Pr | H | Ph-4-Cl | —CONH$_2$ | H |
| Pr | Pr | H | Ph-2-Cl | Me | H |
| Pr | Pr | —CH$_2$OH | Ph-4-F | H | Me |
| Pr | Pr | H | 3-Py | H | H |
| Pr | Pr | H | 3-Thi | Me | H |
| Pr | Pr | H | 2-Fur | Et | Me |
| Me | Ph | H | Ph-4-F | H | H |
| Me | Ph-2-F | H | Ph | Me | H |
| Me | Ph-3-Cl | H | Ph | Me | H |
| Me | Ph | Me | Ph | Me | H |
| Me | Ph | H | Ph | Et | Me |
| Me | Ph | —CH$_2$OH | Ph-3-F | Me | H |
| Me | Ph | H | Ph | —CONH$_2$ | H |
| Me | Ph | H | Ph | 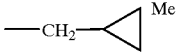 | Me |
| Me | —CH$_2$Ph | H | 4-Py | Et | H |
| Me | —CH$_2$CH$_2$Ph | H | Ph | Et | H |
| Et | Ph-3-Cl | H | Ph-4-F | H | H |
| Et | Ph-4-F | H | Ph | H | H |
| Et | Ph | Me | Ph-4-Cl | H | H |
| Et | Ph | H | Ph-4-F | Me | H |
| Et | Ph | H | Ph | —CONH$_2$ | H |
| Et | Ph | H | 3-Thi | H | H |
| Et | Ph | H | 4-Py | Me | H |
| Pr | Ph | H | Ph-4-F | Me | H |
| Pr |  | H | Ph-4-Cl | Me | H |

TABLE 2-continued

| R¹ | R² | R³ | A | X | W |
|---|---|---|---|---|---|
| cyclopropyl | —CH₂Ph | H | Ph | Me | H |
| —CH₂-cyclopropyl | —CH₂Ph | H | Ph | Me | H |

The compounds of the present invention may be prepared, for example, by the following processes.

Process (a)

The compound of the formula (I) wherein Y is a hydrogen atom, a lower alkyl group, a cycloalkyl group, a cycloalkyl-lower alkyl group, a lower alkenyl group, or a substituted or unsubstituted phenyl-lower alkyl group may be prepared by reacting a compound of the formula (II):

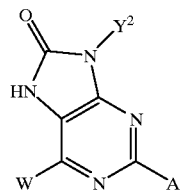

(II)

wherein

A, W and $Y^2$ are the same as defined above, with a compound of the formula (III):

$$Z-CH(R^3)-CON(R^1)(R^2) \quad (III)$$

wherein Z is a leaving atom or a leaving group, and $R^1$, $R^2$ and $R^3$ are the same as defined above.

The leaving atom or the leaving group represented by Z in the formula (III) includes an atom or a group which may be removed in the form of HZ together with the hydrogen atom of the NH moiety of the compound (II) under the reaction conditions, for example, a halogen atom (e.g., chlorine, bromine, iodine), a lower alkylsulfonyloxy group (e.g., methanesulfonyloxy), a trihalogenomethanesulfonyloxy group (e.g., trifluoromethanesulfonyloxy), and an arylsulfonyloxy group (e.g., benzenesulfonyloxy, p-toluenesulfonyloxy).

The reaction of the compound (II) and the compound (III) is carried out in the presence of a base under atmospheric pressure or under pressure in a suitable solvent or without a solvent. The solvent includes, for example, toluene, xylene, dimethoxyethane, 1,2-dichloroethane, acetone, methyl ethyl ketone, dioxane, diglyme, ethyl acetate, dimethylformamide, and dimethylsulfoxide. The base includes, for example, sodium hydride, triethylamine, potassium carbonate, and sodium carbonate. The reaction is usually carried out at a temperature from about −10° C. to about 150° C., preferably at a temperature from about 10° C. to about 70° C.

When $R^1$ and/or $R^3$ of the formula (III) are a hydroxy-lower alkyl group, then said hydroxy-lower alkyl group may preferably be protected by a protecting group which can be removed by hydrogenolysis. Such protecting groups include, for example, benzyloxy, 4-chlorobenzyloxy, 3-bromobenzyloxy, 4-fluorobenzyloxy, 4-methylbenzyloxy, and 4-methoxybenzyloxy. These protecting groups may easily be converted into a hydroxy group by a conventional hydrogenolysis. Beside, when $R^1$ and/or $R^3$ in Processes (b) to (e) as described below are a hydroxy-lower alkyl group, it is preferable to protect these groups likewise, then to remove the protecting groups to give the desired compounds.

The compound of the formula (III) may be prepared by a conventional method, for example, by the method disclosed in Japanese Patent First Publication (Kokai) 64/1987, or a modified method thereof.

The starting compound (II) is prepared, for example, by the processes as shown in the following Route A or Route B.

Route A

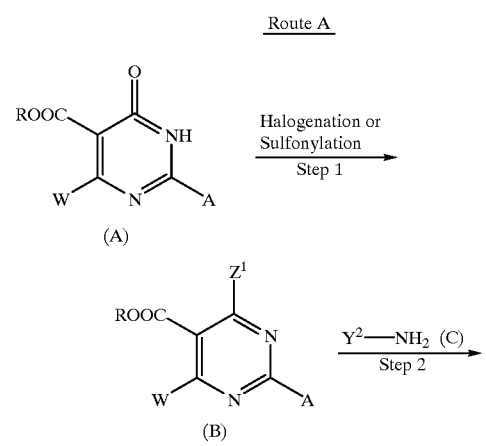

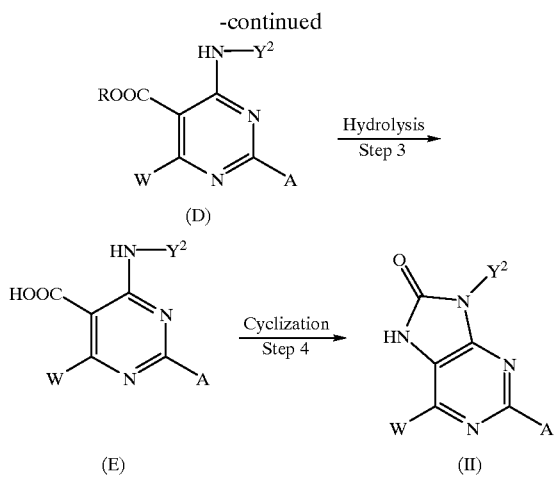

wherein
R is a lower alkyl group, $Z^1$ is a halogen atom, or an arylsulfonyloxy group or alkanesulfonyloxy group such as p-toluene-sulfonyloxy group, a methanesulfonyloxy group, or a trifluoromethanesulfonyloxy group, and A, W and $Y^2$ are the same as defined above.

Route B

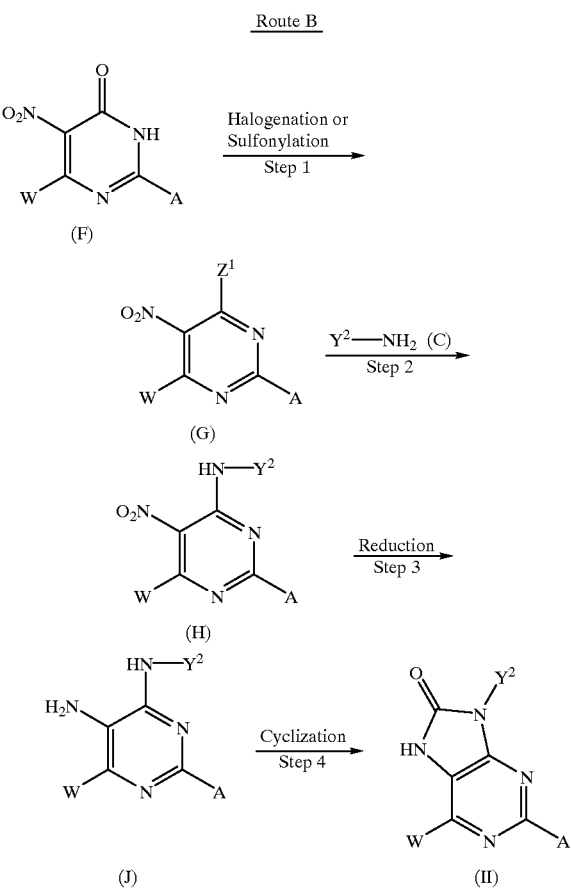

wherein A, W, $Y^2$ and $Z^1$ are the same as defined above.

Step 1: Halogenation or Sulfonylation

The halogenation is carried out by reacting the compound (A) or the compound (F) with a halogenating agent (e.g., phosphorus oxychloride, phosphorus tribromide). The sulfonylation is carried out, for example, by reacting the compound (A) or the compound (F) with a sulfonylating agent (e.g., methanesulfonyl chloride, p-toluenesulfonyl chloride, trifluoromethanesulfonyl chloride).

Step 2: Amination

The reaction of the compound (B) or the compound (G) with the compound (C) is carried out under atmospheric pressure or under pressure in a suitable solvent or without a solvent.

The solvent includes, for example, aromatic hydrocarbons (e.g., toluene, xylene), ketones (e.g., methyl ethyl ketone, methyl isobutyl ketone), ethers (e.g., dioxane, diglyme), alcohols (e.g., ethanol, isopropanol, butanol), acetonitrile, dimethylformamide, and dimethylsulfoxide. The reaction is preferably carried out in the presence of a base, and the base includes, for example, alkali metal carbonates (e.g., sodium carbonate, potassium carbonate), alkali metal hydrogen carbonates (e.g., sodium hydrogen carbonate, potassium hydrogen carbonate), and tertiary amines (e.g., triethylamine), but the excess amount of the compound (C) may be used instead of a base. The reaction temperature varies according to the kinds of the starting compounds or the reaction conditions, but it is usually in the range of about 0° C. to about 200° C., more preferably in the range of about 20° C. to about 100° C.

Step 3 of Route A: Hydrolysis

The hydrolysis is carried out by a conventional method, for example, by contacting with water in a suitable solvent under acidic or basic conditions. The solvent includes, for example, alcohols (e.g., methanol, ethanol, isopropanol), dioxane, water, and a mixture of these solvents. The acid includes, for example, mineral acids (e.g., hydrochloric acid, sulfuric acid), and organic acids (e.g., formic acid, acetic acid, propionic acid, and oxalic acid). The base includes, for example, alkali metal hydroxides (e.g., sodium hydroxide, potassium hydroxide), and alkali metal carbonates (e.g., sodium carbonate, potassium carbonate). The reaction is usually carried out at a temperature from about 20° C. to 100° C.

Step 3 of Route B: Reduction

The reduction is carried out by a conventional method, for example, by reacting with hydrogen in a suitable solvent in the presence of a catalyst such as palladium-carbon, Raney nickel, platinum oxide, etc. The reduction is also carried out by using a combination of a metal (e.g., tin, zinc, iron) or a metal salt (e.g., stannous chloride) and an acid (e.g., hydrochloric acid, acetic acid), or by using iron or stannous chloride alone. The solvent includes, for example, alcohols (e.g., ethanol, methanol), water, acetic acid, dioxane, tetrahydrofuran. The reaction is usually carried out at a temperature from about 0° C. to about 80° C., under atmospheric pressure or under pressure.

Step 4: Cyclization

The cyclization reaction is carried out in the same manner as explained in Process (b) or Process (C) as described below.

The starting compounds (A) and (F) may be commercially available ones, or can be prepared by a conventional method, for example, by the methods disclosed in J. Am. Chem. Soc., 74, 842 (1952); Chem. Ber., 95, 937 (1962); J. Org. Chem., 29, 2887 (1964); J. Med. Chem., 35, 4751 (1992); J. Org. Chem., 58, 4490 (1993); Synthesis, 86 (1985), or the methods disclosed in Reference Examples 1, 11 and 15 as described below, or a modified method thereof.

Process (b)

The compound of the formula (I) wherein X is a hydrogen atom, and Y is a group of the formula (Q) is prepared by reacting a compound of the formula (IV):

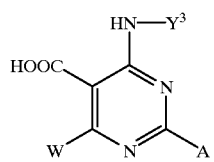

(IV)

wherein
$Y^3$ is the group represented by the above formula (Q), and A and W are the same as defined above, with an azide compound.

The azide compound used in this process includes, for example, diphenylphosphoryl azide, sodium azide.

The reaction is carried out in the presence of a base under atmospheric pressure or under pressure in a suitable solvent or without a solvent. The solvent includes, for example, toluene, xylene, dimethoxyethane, 1,2-dichloroethane, acetone, methyl ethyl ketone, dioxane, diglyme, ethyl acetate, dimethylformamide, and dimethylsulfoxide. The base includes, for example, triethylamine, potassium carbonate, and sodium carbonate. The reaction is usually carried out at a temperature from about 10° C. to about 150° C., preferably at a temperature from about 30° C. to about 120° C.

The starting compound (IV) can be prepared by using the compound (C) in Route A that is $Y^3$—$NH_2$, and the compound (B), by the methods of Step 2 and Step 3 as shown in Route A. Moreover, the starting compound (IV) is also prepared by using the compound (B) in Route A and an amino acid, and introducing a substituted amino group on the 4-position of the pyrimidine ring by the method of Step 2 of Route A, amidating thereof by the method disclosed in Process (e) as described below, and if necessary, by alkylating the product. The detailed procedures are explained in the following Reference Example 63.

Process (c)

The compound of the formula (I) wherein X is a hydrogen atom, and Y is a group of the formula (Q) is prepared by reacting a compound of the formula (V):

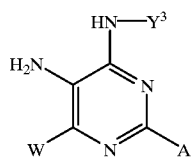

(V)

wherein
A, W and $Y^3$ are the same as defined above, with urea, a carbonyldiimidazole or a diethyl carbonate.

The reaction is carried out in a suitable solvent or without a solvent. The solvent includes, for example, tetrahydrofuran, toluene, dimethylsulfoxide, and ethyleneglycol. The reaction is usually carried out at a temperature from about 20° C. to about 250° C., preferably at a temperature from about 60° C. to about 220° C.

The starting compound (V) is prepared by using the compound (C) in Route B that is $Y^3$—$NH_2$, and the compound (G), by the methods of Step 2 and Step 3 as shown in Route B.

Process (d)

The compound (1) wherein X is a hydrogen atom or the groups other than the group of the formula (Q), and Y is the group of the formula (Q) is prepared by reacting the compound (VI):

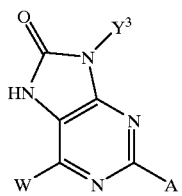

(VI)

wherein
A, W and $Y^3$ are the same as defied above, which is obtained in the above Process (b), with a compound of the formula (VII):

$$Z-X^2 \tag{VII}$$

wherein $X^2$ is a hydrogen atom or the same groups for X except for the group of the formula (Q), and Z is the same as defined above.

The reaction is carried out in the same manner as in Process (a).

The starting compound (VII) may be commercially available ones, or can be prepared by a conventional method.

Process (e)

The compound (I) wherein X is a group of the formula (Q) is prepared by reacting a compound of the formula (VIII):

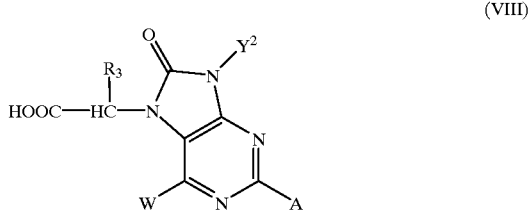

(VIII)

wherein
A, $R^3$, W and $Y^2$ are the same as defined above, or a reactive derivative thereof, with a compound of the formula (IX):

$$HN(R^{13})(R^{23}) \tag{IX}$$

wherein $R^{13}$ and $R^{23}$ are each a hydrogen atom or the same groups for $R^1$ and $R^2$ as defined above, respectively, and when one of $R^{13}$ and $R^{23}$ is a hydrogen atom, then further reacting the product with a compound of the formula (X):

$$R^{24}-Z \tag{X}$$

or the formula (XI):

$$R^{14}-Z \tag{XI}$$

wherein $R^{24}$ is a lower alkyl group, a cycloalkyl group, or a substituted or unsubstituted phenyl-lower alkyl group, $R^{14}$ is a lower alkyl group, a lower alkenyl group, a cycloalkyl group, a cycloalkyl-lower alkyl group, or a hydroxy-lower alkyl group, and Z is the same as defined above, provided that when $R^{13}$ is a hydrogen atom, then reacting with the compound (X), and when $R^{23}$ is a hydrogen atom, then reacting with the compound (XI).

The reactive derivative of the compound (VIII) includes, for example, a lower alkyl ester (especially, methyl ester), an active ester, an acid anhydride, and an acid halide (especially, an acid chloride). The active ester includes, for example, p-nitrophenyl ester, 2,4,5-trichlorophenyl ester, and N-hydroxysuccinimide ester. The acid anhydride includes, for example, a symmetric acid anhydride and a mixed acid anhydride. The mixed acid anhydride includes, for example, a mixed acid anhydride with an alkyl chlorocarbonate such as ethyl chlorocarbonate, and isobutyl chlorocarbonate, a mixed acid anhydride with an aralkyl chlorocarbonate such as benzyl chlorocarbonate, a mixed acid anhydride with an aryl chlorocarbonate such as phenyl chlorocarbonate, and a mixed acid anhydride with an alkanoic acid such as isovaleric acid and pivalic acid.

When the compound (VIII) per se is used, the reaction can be carried out in the presence of a condensing agent such as N,N'-dicyclohexylcarbodiimide, 1-ethyl-3-(3-dimethylaminopropyl)-carbodiimide hydrochloride, N,N'-carbonyldiimidazole, N,N'-carbonyl-disuccinimide, 1-ethoxycarbonyl-2-ethoxy-1,2-dihydroquinoline, diphenylphosphoryl azide, propanesulfonic anhydride, and benzotriazol-1-yloxy-tris(dimethylamino)phosphonium.hexafluorophosphate.

The reaction of the compound (VIII) or a reactive derivative thereof with the compound (IX) is carried out in a solvent or without a solvent. The solvent varies according to the kinds of the starting compounds, etc., and includes, for example, aromatic hydrocarbons (e.g., benzene, toluene, xylene), ethers (e.g., diethyl ether, tetrahydrofuran, dioxane), halogenated hydrocarbons (e.g., methylene chloride, chloroform), alcohols (e.g., ethanol, isopropanol), ethyl acetate, acetone, acetonitrile, dimethylformamide, dimethylsulfoxide, ethylene glycol, water, etc., and these solvents may be used alone, or in the form of a mixture of two or more solvents. The reaction is carried out in the presence of a base if necessary, and the base includes, for example, alkali metal hydroxides (e.g., sodium hydroxide, potassium hydroxide), alkali metal carbonates (e.g., sodium carbonate, potassium carbonate), alkali metal hydrogen carbonates (e.g., sodium hydrogen carbonate, potassium hydrogen carbonate), and organic bases such as triethylamine, tributylamine, diisopropylethylamine, N-methylmorpholine, but the excess amount of the compound (IX) may be used instead of a base. The reaction temperature varies according to the kinds of the starting compounds, but it is usually in the range of about −30° C. to about 200° C., preferably in the range of about −10° C. to about 150° C.

The reaction of the product obtained in the reaction between the compound (VIII) and the compound (IX), and the compound (X) or the compound (XI) is carried out by the method described in the above Process (a).

The compound (VIII) is prepared by reacting a compound of the formula (II):

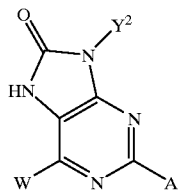

(II)

wherein
A, W and $Y^2$ are the same as defined above, with a compound of the formula (XII):

$Z^1$—CH($R^3$)—COOR (XII)

wherein R, $R^3$ and $Z^1$ are the same as defined above, followed by subjecting the product to hydrolysis in a conventional manner.

The reaction is carried out in the same manner as in Process (a).

The compound (X) and the compound (XI) may be commercially available ones, or can be prepared by a conventional method.

The present compounds can also be prepared by the following methods.

The compound (I) wherein W is a lower alkoxy group is prepared by reacting a compound of the formula (I) wherein W is a halogen atom with a metal lower alkylate, and the detailed procedures thereof are explained in Example 46.

The compound (I) wherein W is a mono- or di-lower alkylamino group is prepared by reacting a compound of the formula (I) wherein W is a halogen atom with a mono- or di-lower alkylamine, and the detailed procedures thereof are explained in Example 47.

The compound (I) wherein the phenyl group is substituted by a hydroxy group is prepared by treating a compound of the formula (I) wherein the phenyl group is substituted by a methoxy group with boron tribromide or hydrogen bromide, and the detailed procedures thereof are explained in Example 174.

The desired compounds obtained in the above Processes can be isolated and purified by a conventional method such as chromatography, recrystallization, re-precipitation, etc. The compound (I) which shows basicity enough to form an acid addition salt thereof is converted into an acid addition salt thereof by treating it with various acids by a conventional method.

Various stereoisomers of the compound (I) can be separated and purified by a conventional method such as chromatography, etc.

The pharmacological activities of the present compounds are explained by the following pharmacological experiments on the representative compounds of the present invention.

Experiment 1: Central ($\omega_1, \omega_2$) and Peripheral ($\omega_3$) Benzodiazepine Receptor Binding Assays BZ$\omega_1$ and BZ$\omega_2$ receptor binding assays and the preparation of receptor membrane fractions therefor were carried out according to the method of Stephens, D. N. et al. [cf., J. Pharmacol. Exp. Ther., 253, 334–343 (1990)], and BZ$\omega_3$ receptor binding assay and the preparation of receptor membrane fraction therefor were done according to the method of Schoemaker, H. [cf, J. Pharmacol. Exp. Ther., 225, 61–69 (1983)] each with slight modification.

Receptor membrane fractions for $\omega_1$, $\omega_2$ and $\omega_3$ were prepared from the cerebellum ($\omega_1$), spinal cord ($\omega_2$) or kidney ($\omega_3$) in 7–8 week old male rats of Wistar strain, respectively, by the procedure described below.

After the cerebellum or spinal cord was homogenized with 20 volumes of ice-cold 50 mM Tris-citrate buffer (pH 7.1), the homogenate was centrifuged for 15 minutes at 40,000 g. The pellet obtained was washed 4 times by the same procedure, and frozen and stored for 24 hours at −60° C. The resulting pellet, after being thawed, washed with the buffer and centrifuged, was suspended in the buffer I for the binding assay (50 mM Tris-HCl buffer containing 120 mM NaCl, 5 mM KCl, 2 mM CaCl$_2$ and 1 mM MgCl$_2$; pH 7.4) and the suspension thus obtained (containing 1 g wet tissue/40 ml) was used for the BZ$\omega_1$ and BZ$\omega_2$receptor binding assays. On the other hand, the kidney was homogenized with 20 volumes of the ice-cold buffer II for the binding assay (50 mM Na-K phosphate buffer containing 100 mM NaCl; pH 7.4), and the mixture was filtered through 4 sheets of gauze, and centrifuged for 20 minutes at 40,000 g. The pellet obtained was suspended in the buffer II and the suspension (containing 1 g wet tissue/100 ml) was used for the binding assay as $BZ\omega_3$ receptor membrane source.

[$^3$H] Flumazenil (Ro 15-1788) (final concentration: 0.3 nM for $\omega_1$, and 1 nM for $\omega_2$) and flunitrazepam (final concentration: 10 $\mu$M) were used for the $BZ\omega_1$ or $BZ\omega_2$ receptor binding assays as the isotope-labeled and unlabeled ligands, respectively. For the $BZ\omega_3$ receptor binding assay, [$^3$H] 4'-chlorodiazepam (7-chloro-1,3-dihydro-1-methyl-5-(4-chlorophenyl)-2H-1,4-diazepin-2-one) (Ro 5-4864) (final concentration: 0.5 nM) and diazepam (final concentration: 100 $\mu$M) were used as the isotope-labeled and unlabeled ligands, respectively. Incubation was performed for 30 minutes at 37° C. in the $BZ\omega_1$ or $BZ\omega_2$ receptor binding assays, and for 150 minutes at 0° C. in the $BZ\omega_3$ receptor binding assay. The $BZ\omega_1$ or $BZ\omega_2$ receptor binding assays were carried out in the presence of bicuculline (final concentration: 100 $\mu$M).

The binding assay was performed by the following procedure. After adding each test compound at certain known concentrations, a [$^3$H] ligand, and the buffer I or II to each test tube, each assay was started by addition of membrane preparation (total volume of 1 ml). After incubation, the assay was terminated by filtration with suction through a Whatman GF/B glass fiber filter using a cell harvester (Brandel, USA). The filters were rapidly washed 3 times with 5 ml of ice-cold 50 mM Tris-HCl buffer (pH 7.7) for $\omega_1$ and $\omega_2$, or the buffer II for $\omega_3$, and transferred to scintillation vials containing 10 ml liquid scintillation cocktail (ACS-II, Amersham, USA). After being allowed to stand for a specific period, retained radioactivity was counted by a liquid scintillation spectrometer. Specific binding of [$^3$H] ligands was calculated as the difference between amounts of radioactivity bound in the presence and absence of excess unlabeled ligands. The concentration of the test compounds causing 50% inhibition of specific binding of the [3H] ligand ($IC_{50}$) was determined by probit analysis. The results are shown in Table 3. It is noted that the compounds as listed in Table 3 had affinity for the $BZ\omega_1$ and $BZ\omega_2$ receptors with $IC_{50}$ values larger than 1000 nM.

TABLE 3

| Test Comp. | $\omega_3$ $IC_{50}$(nM) | Test Comp. | $\omega_3$ $IC_{50}$(nM) |
|---|---|---|---|
| 1* | 2.0 | 83 | 1.3 |
| 2 | 1.2 | 94 | 2.7 |
| 4 | 1.6 | 97 | 0.35 |
| 5 | 1.3 | 99 | 1.4 |
| 6 | 2.0 | 101 | 1.3 |
| 10 | 1.0 | 103 | 0.8 |
| 11 | 2.4 | 106 | 1.2 |
| 12 | 1.5 | 107 | 0.66 |
| 13 | 2.9 | 112 | 0.73 |
| 26 | 2.3 | 113 | 0.97 |
| 29 | 4.5 | 114 | 0.97 |
| 37 | 2.8 | 116 | 2.1 |
| 39 | 1.3 | 136 | 0.66 |
| 40 | 1.6 | 137 | 1.3 |
| 48 | 0.68 | 140 | 0.87 |
| 49 | 1.4 | 146 | 0.85 |
| 50 | 0.79 | 147 | 1.1 |
| 51 | 1.2 | 150 | 0.81 |
| 54 | 0.83 | 151 | 2.3 |
| 56 | 1.4 | 156 | 0.67 |
| 69 | 0.55 | 157 | 1.1 |
| 71 | 0.43 | 161 | 1.1 |
| 73 | 1.7 | 162 | 1.1 |

TABLE 3-continued

| Test Comp. | $\omega_3$ $IC_{50}$(nM) | Test Comp. | $\omega_3$ $IC_{50}$(nM) |
|---|---|---|---|
| 74 | 0.99 | 163 | 0.73 |
| 75 | 1.3 | 166 | 1.2 |
| 77 | 2.4 | 170 | 1.8 |
| 81 | 5.0 | 172 | 3.5 |

*: The compound of Example 1 (hereinafter, the test compound numbers mean the compounds of the corresponding Examples in the same way)

The compounds listed in Table 3 strongly bind to the $BZ\omega_3$ receptor, but had affinity for the $BZ\omega_1$ and $BZ\omega_2$ receptors with the $IC_{50}$ value larger than 1000 nM. Therefore, it is apparent that the compounds of the present invention have potent and highly selective affinity for the $BZ\omega_3$ receptor.

Experiment 2: Light and Dark Box Test (Anti-anxiety Effect)

Anti-anxiety effect of test compounds was examined in a box with light and dark compartments according to the method of Crawley, J. and Goodwin, F. K. [cf., Pharmacol. Biochem. Behav., 13, 167–170 (1980)] with slight modification.

Light and dark box test is a useful, simple and handy method for behaviorally and pharmacologically examining anti-anxiety effect of the drugs, by utilizing the habit of rodents such as mice and rats, etc. which prefer to stay in a dark place, and regarding as positive drug effect the increase of the relative stay of the animals in the light compartment which is an uncomfortable place for the animals. A number of drugs such as cholecystokinin B type receptor antagonists and benzodiazepine drugs, show positive effect in this test.

Light and dark box test was carried out using the test box device (35×17×15 cm) which comprises: a light compartment (20×17×15 cm) consisting of transparent acrylic plates and highly illuminated by an incandescent lamp (1,700 lux); a dark compartment (15×17×15 cm) being made of black acrylic plates connected to the light compartment; and at the boundary of compartments, an opening (4.4×5.0 cm) in which mice can go through freely between two compartments.

Male mice of Std-ddY strain weighing 25–30 g were used in a group of 10. Each trial was started by placing a mouse in the center of the light compartment 30 minutes after oral administration of a test compound, and the time spent by the mouse in the light compartment during a 5 minute observation period was measured, and the rate of the stay of mice in the light compartment to the whole time spent in the experiment was calculated (rate of light compartment stay, %).

The anti-anxiety effect of the test compound was represented by the minimum effective dose (MED) at which the increasing rate of the relative stay in the light compartment was regarded as statistically significant (Dunnett test, significance level: 5%). The results are shown in Table. 4.

TABLE 4

| Test Comp. | Anti-anxiety effect MED (mg/kg) |
|---|---|
| 1* | 0.001 |
| 2 | 0.001 |
| 5 | 0.001 |
| 12 | 0.01 |
| 28 | 0.01 |

TABLE 4-continued

| Test Comp. | Anti-anxiety effect MED (mg/kg) |
|---|---|
| 30 | 1.0 |
| 50 | 0.1 |
| 106 | 0.001 |
| 107 | 0.001 |
| 116 | 0.01 |
| 136 | 0.003 |
| 137 | 0.001 |
| 146 | 0.003 |
| 147 | 0.001 |
| 163 | 0.1 |

*: The compound of Example 1 (hereinafter, the test compound numbers mean the compounds of the corresponding Examples in the same way)

The present compounds as listed in Table 4 showed anti-anxiety effect at doses of 1 mg/kg or below, and especially the compounds of Examples 1, 2, 5, 106, 107, 136, 137, 146 and 147 showed anti-anxiety effect even at a low dose of 0.001–0.003 mg/kg.

Experiment 3: Isoniazid-induced Clonic Convulsion Test (Anti-convulsant Effect)

Isoniazid inhibits glutamate decarboxylase that catalyzes GABA biosynthesis, decrease brain GABA levels, and induces clonic convulsion. According to the method of Auta, J. et al. [cf., J. Pharmacol. Exp. Ther., 265, 649–656 (1993)] with slight modification, antagonistic effects of the test compounds on isoniazid-induced clonic convulsion were examined. Many drugs, which directly or indirectly enhance $GABA_A$ receptor function, are known to exhibit positive effect in this test. Such drugs are BZ receptor agonists represented by diazepam, neurosteroids such as allopregnanolone, allotetrahydro-deoxycorticosterone (THDOC) and $BZ\omega_3$ receptor agonists, which enhance the synthesis of neurosteroids.

Male mice of Std-ddY strain weighing 22–24 g were used in a group of 6. Thirty minutes after oral administration of the test compounds, mice were injected with isoniazid (200 mg/kg) subcutaneously, and immediately thereafter, the mice were placed individually in plastic observation cages. The onset time of clonic convulsion was measured (cut-off time: 90 minutes). The latency in the control group was about 40 minutes.

Anti-isoniazid effect of the test compounds was expressed by the dose, which prolonged the onset time by 25% compared to that in the vehicle group ($ED_{25}$). The $ED_{25}$ value was calculated according to the Probit method. The results are shown in Table 5.

TABLE 5

| Test Comp. | Anti-convulsant effect $ED_{25}$(mg/kg) |
|---|---|
| 106* | 100 |
| 107 | 33.0 |
| 110 | 51.0 |
| 112 | 73.6 |

*: The compound of Example 106 (hereinafter, the test compound numbers mean the compounds of the corresponding Examples in the same way)

Experiment 4: Acute Toxicity

Male mice of Std-ddY strain weighing 25–30 g were used in a group of 10 animals for examining on the compound of Example 1. A test compound was suspended in 0.5% tragacanth and administered orally to the mice at a dose of 2000 mg/kg. Then, lethality of the mice was observed for 7 days after the treatment, and no lethality was found in mice to which the compound of Example 1 was administered.

As is shown in the results of the above pharmacological experiments, the compounds of formula (I) not only show a selective and remarkable affinity for $BZ\omega_3$-receptor in vitro, but also show excellent pharmacological activities such as anti-anxiety effect and anti-convulsant effect, etc. in animal experiments, therefore, they are useful for prophylaxis or treatment of central nervous disorders such as anxiety-related diseases (neurosis, somatoform disorders, anxiety disorders, and others), depression, epilepsy, etc., immuno-neurologic diseases (multiple sclerosis, etc.), and circulatory organs disorders (angina pectoris, hypertension, etc.).

As the compounds showing a selective and remarkable affinity for $BZ\omega_3$ receptor as well as showing potent anti-anxiety activity, the following compounds and pharmaceutically acceptable acid addition salts thereof are exemplified.

(1) N-ethyl-8,9-dihydro-9-methyl-8-oxo-2-phenyl-N-phenyl-7H-purin-7-acetamide (the compound of Example 1)

(2) 8,9-dihydro-9-methyl-N-methyl-8-oxo-2-phenyl-N-phenyl-7H-purin-7-acetamide (the compound of Example 2)

(3) 8,9-dihydro-2-(4-fluorophenyl)-9-methyl-N-methyl-8-oxo-N-phenyl-7H-purin-7-acetamide (the compound of Example 5)

(4) N-ethyl-8,9-dihydro-2-(4-fluorophenyl)-9-methyl-8-oxo-N-phenyl-7H-purin-7-acetamide (the compound of Example 12)

(5) 7,8-dihydro-7-methyl-8-oxo-2-phenyl-N,N-dipropyl-9H-purin-9-acetamide (the compound of Example 106)

(6) 7-ethyl-7,8-dihydro-8-oxo-2-phenyl-N,N-dipropyl-9H-purin-9-acetamide (the compound of Example 107)

(7) N-benzyl-N-ethyl-7,8-dihydro-7-methyl-8-oxo-2-phenyl-9H-purin-9-acetamide (the compound of Example 146)

(8) N-benzyl-7,8-dihydro-N-methyl-7-methyl-8-oxo-2-phenyl-9H-purin-9-acetamide (the compound of Example 136)

(9) N-benzyl-N-ethyl-7,8-dihydro-7-methyl-8-oxo-2-(4-chlorophenyl)-9H-purin-9-acetamide (the compound of Example 147)

(10) N-benzyl-7,8-dihydro-N-methyl-7-methyl-8-oxo-2-(4-chlorophenyl)-9H-purin-9-acetamide (the compound of Example 137)

The compounds of the present invention can be administered either orally, parenterally or rectally. The dose of the compounds of the present invention varies according to the kinds of the compound, the administration routes, the conditions, ages of the patients, etc., but it is usually in the range of 0.01–50 mg/kg/day, preferably in the range of 0.03–5 mg/kg/day.

The compounds of the present invention are usually administered in the form of a pharmaceutical preparation, which is prepared by mixing thereof with a pharmaceutically acceptable carrier or diluent. The pharmaceutically acceptable carrier or diluent may be any conventional ones, which are usually used in the pharmaceutical field, and do not react with the compounds of the present invention. Suitable examples of the pharmaceutically acceptable carrier or diluent are, for example, lactose, inositol, glucose, mannitol, dextran, cyclodextrin, sorbitol, starch, partly pregelatinized starch, white sugar, magnesium metasilicate aluminate, synthetic aluminum silicate, crystalline cellulose, sodium carboxymethylcellulose, hydroxypropyl starch, calcium carboxylmethylcellulose, ion exchange resin, methylcellulose, gelatin, gum arabic, hydroxypropyl cellulose, low substituted hydroxypropyl cellulose, hydroxypropylmethylcellulose, polyvinyl-pyrrolidone, polyvinyl alcohol, alginic acid, sodium alginate, light anhydrous silicic acid, magnesium stearate, talc, carboxyvinyl polymer, titanium oxide, sorbitan fatty acid ester, sodium laurylsulfate, glycerin, glycerin fatty acid ester, purified lanolin, glycerogelatin, polysorbate, macrogol, vegetable oil, wax, propyleneglycol, water, ethanol, polyoxy-ethylene-hydrogenated caster oil (HCO), sodium chloride, sodium hydroxide, hydrochloric acid, disodium hydrogen phosphate, sodium dihydrogen phosphate, citric acid, glutamic acid, benzyl alcohol, methyl p-oxybenzoate, ethyl p-oxybenzoate, etc.

The pharmaceutical preparation is, for example, tablets, capsules, granules, powders, syrups, suspensions, suppositories, injection preparations, etc. These preparations may be prepared by a conventional method. In the preparation of liquids, the compound of the present invention may be dissolved or suspended in water or a suitable other solvent, when administered. Tablets and granules may be coated by a conventional method. In the injection preparations, it is preferable to dissolve the compound of the present invention in water, but if necessary, it may be dissolved by using an isotonic agent or a solubilizer, and further, a pH adjuster, a buffering agent or a preservative may be added thereto.

These preparations may contain the compound of the present invention at a ratio of at least 0.01%, preferably at a ratio of 0.1–70%. These preparations may also contain other therapeutically effective compounds as well.

BEST MODE FOR CARRYING OUT THE INVENTION

The present invention is illustrated in more detail by the following Reference Examples and Examples, but should not be construed to be limited thereto.

The identification of the compounds is carried out by Elementary analysis, Mass spectrum, IR spectrum, NMR spectrum, etc.

The following abbreviations may be used in the following Reference Examples and Examples in order to simplify the description.

[Solvent for recrystallization]

| | | |
|---|---|---|
| A: | | Ethanol |
| AN: | | Acetonitrile |
| CF: | | Chloroform |
| E: | | Diethyl ether |
| M: | | Methanol |
| IP: | | Isopropanol |
| IPE: | | Diisopropyl ether |
| DMF: | | Dimethylformamide |

Reference Example 1

Preparation of ethyl 3,4-dihydro-4-oxo-2-phenylpyrimidine-5-carboxylate

To a mixture of sodium methoxide (16.5 g) and anhydrous ethanol (200 ml) is added benzamidine hydrochloride (16 g) at 0–5° C. The mixture is stirred at 0° C. for 30 minutes, and thereto is added dropwise a solution of diethyl ethoxymethylenemalonate (20 g) in anhydrous ethanol (50 ml) at the same temperature. After the addition, the mixture is stirred at room temperature for 30 minutes, and refluxed for 6 hours. The reaction mixture is concentrated under reduced pressure, and the residue is dissolved in water. To the mixture is added with stirring and drowpise hydrochloric acid at 0–5° C. until the pH value of the mixture is adjusted to pH 4. The precipitates are collected by filtration, washed with water, washed with diethyl ether, and washed with ethanol to give the desired compound (17.5 g).

Reference Examples 2–10

The corresponding starting compounds are treated in the same manner as in Reference Example 1 to give the compounds as listed in Table 6.

TABLE 6

EtOOC–[pyrimidinone ring]–A
(ethyl 3,4-dihydro-4-oxo-2-A-pyrimidine-5-carboxylate)

| Reference Ex. | A |
|---|---|
| 2 | Ph-3-Cl |
| 3 | Ph-4-Cl |
| 4 | Ph-4-F |
| 5 | Ph-4-OMe |
| 6 | Ph-4-$NO_2$ |
| 7 | Ph-4-Me |
| 8 | 3-Pyridyl |
| 9 | 2-Thienyl |
| 10 | 3-Thienyl |

Reference Example 11

Preparation of ethyl 3,4-dihydro-4-oxo-2,6-diphenylpyrimidine-5-carboxylate (1) To a mixture of a 20% solution of sodium ethoxide in ethanol (44.9 g) and ethanol (200 ml) is added benzamidine hydrochloride (10.3 g) at room temperature. The mixture is stirred at the same temperature for two hours, and thereto is added ethyl benzalmalonate (14.0 g), and the mixture is refluxed for three hours. The reaction mixture is concentrated under reduced pressure, and to the residue is added ice-water. To the mixture is added dropwise conc. hydrochloric acid until the pH value of the mixture is adjusted to pH 4. The precipitates are collected by filtration, and washed with water to give crude ethyl 3,4,5,6-tetrahydro-4-oxo-2,6-diphenylpyrimidine-5-carboxylate (15.8 g).

(2) A mixture of the above compound (15.5 g), 2,3-dichloro-2,3-dicyano-p-benzoquinone (13.6 g) and ethanol (300 ml) is stirred at room temperature for four hours. The reaction mixture is concentrated under reduced pressure, and thereto are added water and chloroform. The chloroform layer is separated, dried over anhydrous sodium sulfate, and concentrated under reduced pressure. The residue thus obtained is purified by silica gel column chromatography (eluent; chloroform), and diisopropyl ether is added to the resultant. The precipitates are collected by filtration to give the desired compound (10.7 g).

Reference Examples 12–14

The corresponding starting compounds are treated in the same manner as in Reference Example 11 to give the compounds as listed in Table 7.

TABLE 7

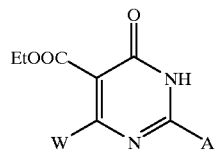

| Reference Ex. | W | A |
|---|---|---|
| 12 | Me | Ph-4-CF$_3$ |
| 13 | Ph | Ph-4-CF$_3$ |
| 14 | Ph-4-CF$_3$ | Ph |

Reference Example 15

Preparation of 5-nitro-2-phenyl-4(3H)-pyrimidinone

To a mixture of sodium methoxide (8 g) and anhydrous ethanol (100 ml) is added benzamidine hydrochloride (11.7 g) at 0° C. The mixture is stirred at 0° C. for 30 minutes, and thereto is added dropwise a solution of crude ethyl 2-(N,N-dimethylaminomethylene)nitroacetate (14 g, which is obtained by heating a mixture of ethyl nitroacetate (10 g) and N,N-dimethylformamide dimethyl acetal (10.7 g) under reflux for three hours, followed by concentrating the mixture under reduced pressure) in anhydrous ethanol (50 ml) at the same temperature. After the addition, the mixture is stirred at room temperature for 30 minutes, and refluxed for 12 hours. The reaction mixture is concentrated under reduced pressure, and to the resultant is added water (150 ml). To the mixture is added dropwise conc. hydrochloric acid at 0° C. until the pH value of the mixture is adjusted to pH 4. The precipitates are collected by filtration, washed with water, and recrystallized from ethanol to give the desired compound (7 g).

M.p. 264–266° C.

Reference Examples 16–18

The corresponding starting compounds are treated in the same manner as in Reference Example 15 to give the compounds as listed in Table 8.

TABLE 8

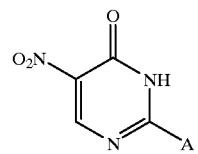

| Reference Ex. | A | M.p. (° C.) | Solvent for recrystallization |
|---|---|---|---|
| 16 | Ph-4-Cl | 218–221 | Ethanol |
| 17 | Ph-3-CF$_3$ | 143–145 | Ethanol |
| 18 | Ph-4-CF$_3$ | 185–188 | Methanol |

Reference Example 19

Preparation of ethyl 4-chloro-2-phenylpyrimidine-5-carboxylate

A mixture of ethyl 3,4-dihydro-4-oxo-2-phenylpyrimidine-5-carboxylate (12 g) and phosphorus oxychloride (22.6 g) is stirred at 90° C. for four hours. The reaction mixture is poured into ice-water, and the mixture is neutralized with 1N aqueous sodium hydroxide solution. The precipitates are collected by filtration, and washed with water to give the desired compound (11 g).

Reference Examples 20–28

The corresponding starting compounds are treated in the same manner as in Reference Example 19 to give the compounds as listed in Table 9.

TABLE 9

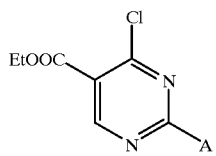

| Reference Ex. | A |
|---|---|
| 20 | Ph-3-Cl |
| 21 | Ph-4-Cl |
| 22 | Ph-4-F |
| 23 | Ph-4-OMe |
| 24 | Ph-4-NO$_2$ |
| 25 | Ph-4-Me |
| 26 | 3-Pyridyl |
| 27 | 2-Thienyl |
| 28 | 3-Thienyl |

Reference Example 29

Preparation of 4-chloro-5-nitro-2-phenylpyrimidine

A mixture of 5-nitro-2-phenyl-4(3H)-pyrimidinone (6 g) and phosphorus oxychloride (8.5 g) is stirred at 90° C. for four hours. After cooling, the reaction mixture is concentrated under reduced pressure, and the residue is dissolved in chloroform. To the mixture is added ice-water, and the mixture is stirred. The mixture is neutralized with 1N aqueous sodium hydroxide solution, and the chloroform layer is separated, dried over anhydrous sodium sulfate, and concentrated under reduced pressure. The residue is recrystallized from ethanol to give the desired compound (5.6 g).

M.p. 160–161° C.

Reference Examples 30–32

The corresponding starting compounds are treated in the same manner as in Reference Example 29 to give the compounds as listed in Table 10.

TABLE 10

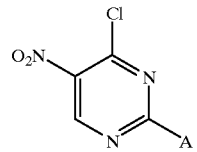

| Reference Ex. | A | M.p. (° C.) | Solvent for recrystal. |
|---|---|---|---|
| 30 | Ph-4-Cl | 144–146 | Isopropanol |
| 31 | Ph-3-CF$_3$ | 89–90 | Isopropanol |
| 32 | Ph-4-CF$_3$ | 77–78 | Isopropanol |

Reference Example 33

Preparation of 4,6-dichloro-5-nitro-2-phenylpyrimidine (1) Using a 20% solution of sodium ethoxide in ethanol (150 g), benzamidine hydrochloride (34.5 g), diethyl malonate (32 g) and ethanol (500 ml), the same procedures as Reference Example 11-(1) are repeated to give crude 4,6-dihydroxy-2-phenylpyrimidine (31.5 g).

(2) To 90% nitric acid (150 ml) is added the above compound (30 g) in portions at 0–5° C., and the mixture is stirred at room temperature for 30 minutes. The reaction mixture is poured into ice-water, and the precipitates are collected by filtration, and washed with water to give crude 4,6-dihydroxy-5-nitro-2-phenylpyrimidine (32 g).

(3) To a mixture of the above compound (8 g) and dimethylaniline (4 g) is added dropwise phosphorus oxychloride at room temperature. After the addition, the mixture is refluxed for three hours, and the reaction mixture is poured into ice-water. The precipitates are collected by filtration, and washed with water to give the desired compound (8.7 g).

Reference Example 34

Preparation of 4-methylamino-2-phenylpyrimidine-5-carboxylic acid (1) A mixture of ethyl 4-chloro-2-phenylpyrimidine-5-carboxylate (10 g), methylamine hydrochloride (2.8 g), triethylamine (8.5 g) and isopropanol (100 ml) is refluxed for six hours. The reaction mixture is concentrated under reduced pressure, and to the residue are added chloroform and water. The chloroform layer is separated, dried over anhydrous sodium sulfate, and concentrated under reduced pressure. The residue is purified by silica gel column chromatography (eluent; chloroform), and recrystallized from ethanol to give ethyl 4-methylamino-2-phenylpyrimidine-5-carboxylate (8 g).

(2) A mixture of the above compound (8 g), 1N aqueous sodium hydroxide solution (150 ml) and ethanol (50 ml) is refluxed for two hours. The reaction mixture is concentrated under reduced pressure, and the residue is dissolved in ice-water, and thereto is added conc. hydrochloric acid until the pH value of the mixture is adjusted to pH 1. The precipitated crystals are collected by filtration, washed with water, and washed with ethanol to give the desired compound (7.3 g).

Reference Examples 35–50

The corresponding starting compounds are treated in the same manner as in Reference Example 34 to give the compounds as listed in Table 11.

TABLE 11

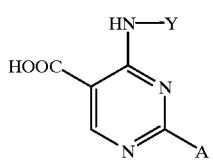

| Reference Ex. | Y | A |
|---|---|---|
| 35 | Me | Ph-3-Cl |
| 36 | Me | Ph-4-Cl |
| 37 | Me | Ph-4-F |
| 38 | Me | Ph-4-OMe |
| 39 | Me | Ph-4-NO$_2$ |
| 40 | Me | Ph-4-Me |
| 41 | Me | 3-Pyridyl |
| 42 | Me | 2-Thienyl |
| 43 | Me | 3-Thienyl |

TABLE 11-continued

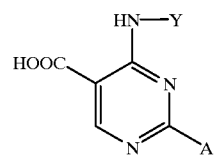

| Reference Ex. | Y | A |
|---|---|---|
| 44 | —CH$_2$Ph | Ph |
| 45 | —CH$_2$CON(Pr)$_2$ | Ph |
| 46 | —CH$_2$CON(Pr)$_2$ | Ph-3-Cl |
| 47 | —CH$_2$CON(Pr)$_2$ | Ph-4-F |
| 48 | —CH$_2$CON(Pr)$_2$ | Ph-4-OMe |
| 49 | —CH$_2$CON(Pr)$_2$ | Ph-4-NO$_2$ |
| 50 | —CH$_2$CON(Me)Ph | 3-Pyridyl |

Reference Example 51

Preparation of 2-phenyl-4-propylaminopyrimidine-5-carboxylic acid (1) A mixture of ethyl 3,4-dihydro-4-oxo-2-phenylpyrimidine-5-carboxylate (9.8 g), triethylamine (10.1 g) and dimethylformamide (20 ml) is added dropwise a solution of p-toluenesulfonyl chloride (8.4 g) in dimethylformamide (20 ml) at room temperature, and the mixture is stirred at the same temperature for 10 minutes. To the reaction mixture is added dropwise a solution of propylamine (2.8 g) in dimethylformamide (20 ml), and the mixture is stirred at room temperature for one hour. To the reaction mixture are added chloroform and water, and the chloroform layer is separated, dried over anhydrous sodium sulfate, and concentrated under reduced pressure to give crude ethyl 2-phenyl-4-propylaminopyrimidine-5-carboxylate (11 g).

(2) A mixture of the above compound (11 g), 1N aqueous sodium hydroxide solution (100 ml) and ethanol (100 ml) is refluxed for two hours. The reaction mixture is concentrated under reduced pressure, and the residue is dissolved in ice-water, and thereto is added conc. hydrochloric acid until the pH value of the mixture is adjusted to pH 1. The precipitated crystals are collected by filtration, washed with water, and washed with ethanol to give the desired compound (9.6 g).

Reference Examples 52–62

The corresponding starting compounds are treated in the same manner as in Reference Example 51 to give the compounds as listed in Table 12.

TABLE 12

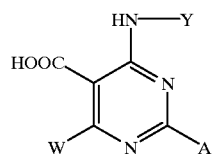

| Reference Ex. | W | Y | A |
|---|---|---|---|
| 52 | H | Et | Ph |
| 53 | H | H | Ph |
| 54 | Ph | Me | Ph |

TABLE 12-continued

HOOC, HN—Y, W, N, A (structure)

| Reference Ex. | W | Y | A |
|---|---|---|---|
| 55 | Me | Me | Ph-4-CF$_3$ |
| 56 | Ph | Me | Ph-4-CF$_3$ |
| 57 | H | —CH$_2$CON(Me)$_2$ | Ph |
| 58 | H | —CH$_2$CON(Et)$_2$ | Ph |
| 59 | H | —CH$_2$CON(Bu)$_2$ | Ph |
| 60 | H | —CH$_2$CON(Me)Ph | Ph |
| 61 | H | —CH$_2$CON(Et)Ph | Ph |
| 62 | H | —CH$_2$CON(Pr)Ph | Ph |

Reference Example 63

Preparation of 4-(N-benzyl-N-methylcarbamoylmethylamino)-2-phenylpyrimidine-5-carboxylic acid (1) A mixture of ethyl 4-chloro-2-phenylpyrimidine-5-carboxylate (21 g), glycine (6.6 g), trimethylamine (17.8 g) and ethanol (200 ml) is refluxed for four hours. The reaction mixture is concentrated under reduced pressure, and the residue is dissolved in water. To the mixture is added dropwise conc. hydrochloric acid under stirring at 0–5° C. until the value of the mixture is adjusted to pH 4. The precipitates are collected by filtration, and washed with water to give crude N-(5-ethoxycarbonyl-2-phenyl-4-pyrimidinyl)glycine (24 g).
(2) A mixture of the above compound (6 g), N-methylbenzylamine (3.6 g), benzotriazol-1-yloxy-tris(dimethylamino)phosphonium.hexafluorophosphate (hereinafter, referred to as BOP reagent, 13.3 g), triethylamine (3.0 g) and dimethylformamide (100 ml) is stirred at room temperature for one hour. The reaction mixture is concentrated under reduced pressure, and to the residue are added water and chloroform. The chloroform layer is separated, dried over anhydrous magnesium sulfate, and concentrated under reduced pressure. The residue is purified by silica gel column chromatography (eluent; chloroform) to give crude ethyl 4-(N-benzyl-N-methylcarbamoylmethylamino)-2-phenyl-pyrimidine-5-carboxylate (7.8 g).
(3) A mixture of the above compound (7.8 g), 1N aqueous sodium hydroxide solution (100 ml) and ethanol (100 ml) is refluxed for two hours. The reaction mixture is concentrated under reduced pressure, and the residue is dissolved in ice-water. To the mixture is added conc. hydrochloric acid until the pH value of the mixture is adjusted to pH 1. The precipitated crystals are collected by filtration, washed with water, and washed with ethanol to give the desired compound (7.0 g).

Reference Examples 64–70

The corresponding starting compounds are treated in the same manner as in Reference Example 63 to give the compounds as listed in Table 13.

TABLE 13

HOOC, HN—CH$_2$—CO—N(R$^1$)(R$^2$), N, A (structure)

| Reference Ex. | R$^1$ | R$^2$ | A |
|---|---|---|---|
| 64 | Me | —CH$_2$Ph | Ph-4-Cl |
| 65 | Me | —CH$_2$Ph | Ph-4-F |
| 66 | Me | —CH$_2$Ph | Ph-4-OMe |
| 67 | Et | —CH$_2$Ph | Ph |
| 68 | Et | —CH$_2$Ph | Ph-4-Cl |
| 69 | Et | —CH$_2$Ph | Ph-4-F |
| 70 | Et | —CH$_2$Ph | Ph-4-OMe |
| 71 | Me | Bzl-4-F | Ph |
| 72 | Me | Bzl-3-F | Ph |
| 73 | Me | Bzl-2-F | Ph |
| 74 | Me | Bzl-4-Cl | Ph |
| 75 | Me | Bzl-4-OMe | Ph |
| 76 | Et | Bzl-4-F | Ph |
| 77 | Et | Bzl-3-F | Ph |
| 78 | Et | Bzl-2-F | Ph |
| 79 | Et | Bzl-4-Cl | Ph |
| 80 | Et | Bzl-4-OMe | Ph |

Reference Example 81

Preparation of 4-ethylamino-5-nitro-2-phenylpyrimidine

A mixture of 4-chloro-5-nitro-2-phenylpyrimidine (3 g), ethylamine hydrochloride (1.6 g), triethylamine (3.9 g) and isopropanol (60 ml) is refluxed for three hours. The reaction mixture is concentrated under reduced pressure, and to the residue are added chloroform and water. The chloroform layer is separated, dried over anhydrous sodium sulfate, and concentrated under reduced pressure. The residue is purified by silica gel column chromatography (eluent; chloroform), and recrystallized from isopropanol to give the desired compound (2.9 g).

M.p. 136–137° C.

Reference Example 82

Preparation of 4-methylamino-5-nitro-2-(4-trifluoromethylphenyl)pyrimidine

The corresponding starting compounds are treated in the same manner as in Reference Example 81, and the product thus obtained is further recrystallized from isopropanol to give the desired compound.

M.p. 170–172° C.

Reference Examples 83–92

The corresponding starting compounds are treated in the same manner as in Reference Example 81 to give the compounds as listed in Table 14.

TABLE 14

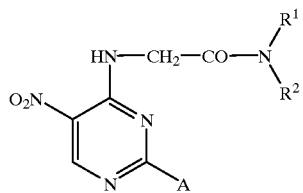

| Reference Ex. | R$^1$ | R$^2$ | A | M.p. (° C.) | Solvent for recrystal. |
|---|---|---|---|---|---|
| 83 | Pr | Pr | Ph | 142–143 | A |
| 84 | Pr | Pr | Ph-4-Cl | 151–152 | A |
| 85 | Me | Me | Ph-3-CF$_3$ | 205–207 | IP |
| 86 | Me | Me | Ph-4-CF$_3$ | 225–226 | A |
| 87 | Me | Ph | Ph | 202–204 | A |
| 88 | Me | Ph-3-Cl | Ph | 147–148 | A |
| 89 | Me | Ph-4-Cl | Ph | 157–158 | A |
| 90 | Me | Ph-4-OMe | Ph | 209–210 | A |
| 91 | Et | Ph | Ph | 205–207 | A |
| 92 | Me | Ph-4-OMe | Ph-4-Cl | 172–173 | A |

Reference Example 93

Preparation of 6-chloro-4-methylamino-5-nitro-2-phenylpyrimidine

The corresponding starting compounds are treated in the same manner as in Reference Example 81 to give the desired compound.

EXAMPLE 1

Preparation of N-ethyl-8,9-dihydro-9-methyl-8-oxo-2-phenyl-N-phenyl-7H-purin-7-acetamide to a mixture of about 60% sodium hydride (oily) (1.4 g) and dimethylformamide (70 ml) is added 7,9-dihydro-9-methyl-2-pheny-8H-purin-8-one (7.0 g) in portions at 0–5° C., and the mixture is stirred at 0° C. for one hour. To the mixture is added dropwise 2-bromo-N-ethyl-N-phenylacetamide (8.3 g) at the same temperature. After the addition, the mixture is stirred at room temperature for three hours. To the reaction mixture are added water and chloroform. The chloroform layer is separated, dried over anhydrous sodium sulfate, and concentrated under reduced pressure. The residue is purified by silica gel column chromatography (eluent; chloroform) and recrystallized from ethanol to give the desired compound (10.3 g).

M.p. 240–242° C.

EXAMPLES 2–44

The corresponding starting compounds are treated in the same manner as in Example 1 to give the compounds as listed in Tables 15 and 16.

TABLE 15

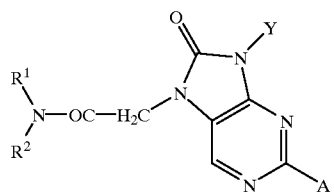

| Ex. | R$^1$ | R$^2$ | Y | A | M.p. (° C.) | Solvent for recrystal. |
|---|---|---|---|---|---|---|
| 2 | Me | Ph | Me | Ph | 147–148 | IP |
| 3 | Me | Ph | Me | Ph-3-Cl | 188–189 | A |
| 4 | Me | Ph | Me | Ph-4-Cl | 188–190 | A |
| 5 | Me | Ph | Me | Ph-4-F | 169–170 | A |
| 6 | Me | Ph | Me | Ph-4-OMe | 176–178 | A |
| 7 | Me | Ph | Me | Ph-4-NO$_2$ | 262–264 | A-CF |
| 8 | Me | Ph | Et | Ph | 160–161 | A |
| 9 | Et | Ph | H | Ph | 281–284 | A |
| 10 | Et | Ph | Me | Ph-3-Cl | 195–196 | IP |
| 11 | Et | Ph | Me | Ph-4-Cl | 174–175 | A |
| 12 | Et | Ph | Me | Ph-4-F | 211–212 | A |
| 13 | Et | Ph | Me | Ph-4-OMe | 179–181 | A |
| 14 | Et | Ph | Me | Ph-4-NO$_2$ | 231–232 | A-CF |
| 15 | Et | Ph | Me | Ph-4-Me | 197–198 | A |
| 16 | Et | Ph | Et | Ph | 165–167 | A |
| 17 | Et | Ph | Pr | Ph | 138–139 | A |
| 18 | Et | Ph | —CH$_2$Ph | Ph | 150–152 | A |
| 19 | Et | Et | Me | Ph | 207–209 | A |
| 20 | Et | Et | Me | Ph-3-Cl | 162–164 | A |
| 21 | Et | Et | Me | Ph-4-Cl | 157–159 | A |
| 22 | Et | Et | Me | Ph-4-F | 124–125 | A |
| 23 | Et | Et | Me | Ph-4-OMe | 137–139 | A |
| 24 | Et | Et | Me | Ph-4-NO$_2$ | 238–240 | A-CF |
| 25 | Et | Et | Et | Ph | 148–150 | A |
| 26 | Pr | Pr | Me | Ph | 133–134 | E |
| 27 | Pr | Pr | Me | Ph-3-Cl | 133–135 | A |
| 28 | Pr | Pr | Me | Ph-4-Cl | 149–150 | A |
| 29 | Pr | Pr | Me | Ph-4-F | 154–155 | A |
| 30 | Pr | Pr | Me | Ph-4-OMe | 120–121 | A |
| 31 | Pr | Pr | Me | Ph-4-NO$_2$ | 186–188 | A-CF |
| 32 | Pr | Pr | Me | Ph-4-CF$_3$ | 150–151 | A |
| 33 | Pr | Pr | Et | Ph | 134–135 | A |
| 34 | Et | Pr | Me | Ph | 150–151 | A |
| 35 | Me | Me | Me | Ph | 204–206 | A |
| 36 | Me | Me | Me | Ph-4-CF$_3$ | 200–202 | A |
| 37 | Me | Ph | Me | 3-Pyridyl | 209–211 | AN |
| 38 | Et | Ph | Me | 3-Pyridyl | 195–196 | AN |
| 39 | Et | Ph | Me | 2-Thienyl | 236–238 | A |
| 40 | Et | Ph | Me | 3-Thienyl | 226–228 | A |

TABLE 16

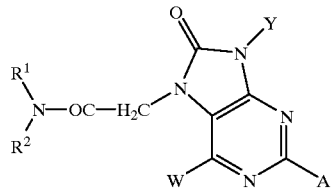

| Ex. | W | R$^1$ | R$^2$ | Y | A | M.p. (° C.) | Sol. for recrystal. |
|---|---|---|---|---|---|---|---|
| 41 | Ph | Et | Ph | Me | Ph | 185–187 | A |
| 42 | Me | Me | Me | Me | Ph-4-CF$_3$ | 217–219 | A |
| 43 | Ph | Me | Me | Me | Ph-4-CF$_3$ | 234–235 | IP |
| 44 | Ph-4-CF$_3$ | Me | Me | Me | Ph | 231–233 | A |

EXAMPLE 45

Preparation of 6-chloro-N-ethyl-8,9-dihydro-9-methyl-8-oxo-2-phenyl-N-phenyl-7H-purin-7-acetamide To a mixture of 6-chloro-7,9-dihydro-9-methyl-2-phenyl-8H-purin-8-one (1.6 g), potassium carbonate (1.0 g) and dimethylformamide (15 ml) is added 2-chloro-N-ethyl-N-phenylacetamide (1.4 g) at room temperature, and the mixture is stirred at the same temperature for two hours. To the reaction mixture is added water, and the precipitates are collected by filtration, washed with water, and purified by silica gel column chromatography (eluent; chloroform), and recrystallized from ethanol to give the desired compound (1.8 g).

M.p. 212–213° C.

EXAMPLE 46

Preparation of N-ethyl-8,9-dihydro-6-methoxy-9-methyl-8-oxo-2-phenyl-N-phenyl-7H-purin-7-acetamide A mixture of 6-chloro-N-ethyl-8,9-dihydro-9-methyl-8-oxo-2-phenyl-N-phenyl-7H-purin-7-acetamide (0.6 g) obtained in Example 45, a 28% solution of sodium methoxide in methanol (0.3 g), methanol (20 ml) and 1,3-dimethyl-2-imidazolidinone (5 ml) is refluxed for four hours. The reaction mixture is concentrated under reduced pressure, and to the residue are added water and chloroform. The chloroform layer is separated, dried over anhydrous sodium sulfate, and concentrated under reduced pressure. The residue is purified by silica gel column chromatography (eluent; chloroform), and recrystallized from ethanol to give the desired compound (0.3 g).

M.p. 173–175° C.

EXAMPLE 47

Preparation of N-ethyl-8,9-dihydro-9-methyl-6-dimethylamino-8-oxo-2-phenyl-N-phenyl-7H-purin-7-acetamide A mixture of 6-chloro-N-ethyl-8,9-dihydro-9-methyl-8-oxo-2-phenyl-N-phenyl-7H-purin-7-acetamide obtained in Example 45 (0.6 g), dimethylamine hydrochloride (0.2 g), triethylamine (0.4 g) and dimethylformamide (20 ml) is stirred at 100° C. for four hours. The reaction mixture is concentrated under reduced pressure, and to the residue are added water and chloroform. The chloroform layer is separated, dried over anhydrous magnesium sulfate, and concentrated under reduced pressure. The residue is purified by silica gel column chromatography (eluent; chloroform), and recrystallized from diisopropyl ether to give the desired compound (0.34 g).

M.p. 179–181° C.

EXAMPLE 48

Preparation of N-benzyl-8,9-dihydro-9-methyl-N-methyl-8-oxo-2-phenyl-7H-purin-7-acetamide (1) A mixture of 7,9-dihydro-9-methyl-2-phenyl-8H-purin-8-one (22.6 g), ethyl chloroacetate (13.5 g), potassium carbonate (15.2 g) and dimethylformamide (250 ml) is stirred at room temperature for one hour. To the reaction mixture are added water and chloroform, and the chloroform layer is separated, dried over anhydrous magnesium sulfate, and concentrated under reduced pressure to give crude ethyl 8,9-dihydro-9-methyl-8-oxo-2-phenyl-7H-purin-7-acetate (26 g).

(2) A mixture of the above product (26 g), 1N aqueous sodium hydroxide solution (500 ml) and ethanol (500 ml) is refluxed for one hour. The reaction mixture is concentrated under reduced pressure, and water is added to the residue. To the mixture is added dropwise conc. hydrochloric acid until the pH value of the mixture is adjusted tb pH 1. The precipitates are collected by filtration, washed with water, and washed with ethanol to give crude 8,9-dihydro-9-methyl-8-oxo-2-phenyl-7H-purin-7-acetic acid (22 g).

(3) A mixture of the above product (1.1 g), methylbenzylamine (0.7 g), BOP reagent (2.6 g), triethylamine (0.6 g) and dimethylformamide (30 ml) is stirred at room temperature for one hour. The reaction mixture is concentrated under reduced pressure, and water and chloroform are added to the residue. The chloroform layer is separated, dried over anhydrous magnesium sulfate, and concentrated under reduced pressure. The residue is purified by silica gel column chromatography (eluent; chloroform), and recrystallized from ethanol and diisopropyl ether to give the desired compound (1.1 g).

M.p. 160–161° C.

EXAMPLES 49–65

The corresponding starting compounds are treated in the same manner as in Example 48 to give the compounds as listed in Table 17.

TABLE 17

| Ex. | $R^1$ | $R^2$ | Y | A | M.p. (° C.) | Solvent. for recrystal. |
|---|---|---|---|---|---|---|
| 49 | Me | —CH$_2$Ph | Me | Ph-4-Cl | 210–211 | A |
| 50 | Me | —CH$_2$Ph | Me | Ph-4-F | 170–171 | A |
| 51 | Me | —CH$_2$Ph | Me | Ph-4-OMe | 205–206 | A |
| 52 | Me | —CH$_2$Ph | Et | Ph | 151–153 | A |
| 53 | Me | —CH$_2$Ph | Pr | Ph | 132–134 | A |
| 54 | Et | —CH$_2$Ph | Me | Ph | 112–115 | A-IPE |
| 55 | Et | —CH$_2$Ph | Me | Ph-4-Cl | 184–186 | A |
| 56 | Et | —CH$_2$Ph | Me | Ph-4-F | 155–157 | A |
| 57 | Et | —CH$_2$Ph | Me | Ph-4-OMe | 181–182 | A |
| 58 | Et | —CH$_2$Ph | Et | Ph | 133–134 | A-IPE |
| 59 | Et | —CH$_2$Ph | Pr | Ph | 114–116 | A |
| 60 | Pr | Ph | Me | Ph | 221–223 | A |
| 61 | Pr | Ph | Et | Ph | 168–170 | A-IPE |
| 62 | Bu | Ph | Me | Ph | 207–209 | A |
| 63 | Bu | Bu | Me | Ph | 138–139 | A |
| 64 | Pent | Pent | Me | Ph | 91–92 | IPE |
| 65 | —(CH$_2$)$_5$— | | Me | Ph | 192–194 | A |

EXAMPLE 66

Preparation of 8,9-dihydro-9-methyl-7-(2,6-dimethylmorpholin-4-yl-carbonylmethyl)-8-oxo-2-phenyl-7H-purine 6-Dimethylmorpholine is treated in the same manner as in Example 48-(3), and the product thus obtained is recrystallized from acetonitrile and diisopropyl ether to give the desired compound.

M.p. 160–161° C.

EXAMPLE 67

Preparation of N-ethyl-N-phenyl-2-(8,9-dihydro-9-methyl-8-oxo-2-phenyl-7H-purin-7-yl)propanamide The same procedures as Example 48 are repeated except that ethyl 2-chloropropionate is used instead of ethyl chloroacetate in Example 48-(1), and N-ethylaniline is used instead of methyl benzylamine in Example 48-(3). The product thus obtained is recrystallized from ethanol to give the desired compound.

M.p. 150–151° C.

EXAMPLE 68

Preparation of 8,9-dihydro-N-(2-hydroxyethyl)-9-methyl-8-oxo-2-phenyl-N-phenyl-7H-purin-7-acetamide (1) A mixture of 8,9-dihydro-9-methyl-8-oxo-2-phenyl-7H-purin-7-acetic acid (3 g) obtained in Example 48-(2), aniline (1.3 g), BOP reagent (5.1 g), triethylamine (1.2 g) and dimethylformamide (20 ml) is stirred at room temperature for two hours. To the reaction mixture is added water, and the precipitates are collected by filtration, and washed with water to give crude 8,9-dihydro-9-methyl-8-oxo-2-phenyl-N-phenyl-7H-purin-7-acetamide (3.5 g).

(2) To a mixture of about 60% sodium hydride (oily) (0.3 g) and dimethylformamide (30 ml) is added the above product (2.5 g) in portions at 0–5° C., and the mixture is stirred at 0° C. for one hour. To the mixture is added dropwise 2-bromoethyl acetate (2.2 g) at the same temperature. After the addition, the mixture is stirred at room temperature for three hours. To the reaction mixture are added water and chloroform. The chloroform layer is separated, dried over anhydrous sodium sulfate, and concentrated under reduced pressure. The residue is purified by silica gel column chromatography (eluent; chloroform), and recrystallized from isopropanol to give N-(2-acetoxyethyl)-8,9-dihydro-9-methyl-8-oxo-2-phenyl-N-phenyl-7H-purin-7-acetamide (0.9 g).

M.p. 158–160° C.

(3) A mixture of the above product (0.9 g), potassium carbonate (0.3 g) and methanol (15 ml) is stirred at room temperature for three hours. To the reaction mixture is added water, and the precipitates are collected by filtration, washed with water, and recrystallized from methanol and acetonitrile to give the desired compound (0.05 g).

M.p. 231–233° C.

EXAMPLE 69

Preparation of N-(4-fluorobenzyl)-8,9-dihydro-9-methyl-N-methyl-8-oxo-2-phenyl-7H-purin-7-acetamide (1) A mixture of 8,9-dihydro-9-methyl-8-oxo-2-phenyl-7H-purin-7-acetic acid (9.1 g) obtained in Example 48-(2), methylamine hydrochloride (3.2 g), BOP reagent (21.2 g), triethylamine (9.7 g), and dimethylformamide (100 ml) is stirred at room temperature for two hours. Water is added to the reaction mixture, and the precipitates are collected by filtration, and washed with water to give crude 8,9-dihydro-9-methyl-N-methyl-8-oxo-2-phenyl-7H-purin-7-acetamide (8.1 g).

(2) To a mixture of about 60% sodium hydride (oily) (0.2 g) and dimethylformamide (30 ml) is added the above product (1.2 g) in portions at 0–5° C., and the mixture is stirred at 0° C. for one hour. To the mixture is added dropwise 4-fluorobenzyl bromide (1.0 g) at the same temperature. After the addition, the mixture is stirred at room temperature for three hours. Water and chloroform are added to the reaction mixture, and the chloroform layer is separated, dried over anhydrous sodium sulfate, and concentrated under reduced pressure. The residue is purified by silica gel column chromatography (eluent; chloroform), and recrystallized from ethanol to give the desired compound (0.6 g).

M.p. 197–199° C.

EXAMPLES 70–78

The corresponding starting compounds are treated in the same manner as in Example 69 to give the compounds as listed in Table 18.

TABLE 18

| Ex. | $R^1$ | $R^2$ | Y | A | M.p. (° C.) | Solvent for recrystal. |
|---|---|---|---|---|---|---|
| 70 | Me | Bzl-3-F* | Me | Ph | 163–164 | A |
| 71 | Me | Bzl-2-F | Me | Ph | 198–199 | A |
| 72 | Me | Bzl-4-Cl | Me | Ph | 183–184 | A |
| 73 | Me | Bzl-4-OMe | Me | Ph | 174–176 | A |
| 74 | Et | Bzl-4-F | Me | Ph | 166–167 | A |
| 75 | Et | Bzl-3-F | Me | Ph | 144–145 | A |
| 76 | Et | Bzl-2-F | Me | Ph | 164–165 | A |
| 77 | Et | Bzl-4-Cl | Me | Ph | 198–199 | A |
| 78 | Et | Bzl-4-OMe | Me | Ph | 155–156 | A |

*In the above Table, Bzl-3-F means 3-fluorobenzyl group.

EXAMPLE 79

Preparation of 7,8-dihydro-8-oxo-2-phenyl-N,N-dipropyl-9H-purin-9-acetamide

To a mixture of 2-phenyl-4-(N,N-dipropylcarbamoylmethylamino)pyrimidine-5-carboxylic acid (10 g) and dimethylformamide (70 ml) is added triethylamine (2.8 g) at room temperature, and the mixture is stirred for 10 minutes, and thereto is added diphenylphosphoryl azide (7.7 g) at the same temperature. The reaction mixture is stirred at 100° C. for two hours, and concentrated under reduced pressure. The residue is poured into ice-water, and the precipitates are collected by filtration, washed with water, and recrystallized from ethanol to give the desired compound (7 g).

M.p. 190–191° C.

EXAMPLES 80–96

The corresponding starting compounds are treated in the same manner as in Example 79 to give the compounds as listed in Table 19.

TABLE 19

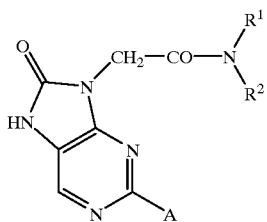

| Ex. | R¹ | R² | A | M.p. (° C.) | Solvent for recrystal. |
|---|---|---|---|---|---|
| 80 | Pr | Pr | Ph-3-Cl | 172–174 | A |
| 81 | Pr | Pr | Ph-4-F | 213–215 | A |
| 82 | Pr | Pr | Ph-4-OMe | 159–160 | A |
| 83 | Pr | Pr | Ph-4-NO₂ | 256–258 | A |
| 84 | Me | Ph | 3-Pyridyl | 268–270 | CF-AN |
| 85 | Et | Et | Ph | 222–224 | A-CF |
| 86 | Me | Me | Ph | >300 | A |
| 87 | Me | —CH₂Ph | Ph | 261–263 | A |
| 88 | Me | —CH₂Ph | Ph-4-Cl | 289–290 | A |
| 89 | Me | —CH₂Ph | Ph-4-F | 286–288 | A |
| 90 | Me | —CH₂Ph | Ph-4-OMe | 240–241 | A |
| 91 | Et | —CH₂Ph | Ph | 212–214 | A |
| 92 | Et | —CH₂Ph | Ph-4-Cl | 264–266 | A |
| 93 | Et | —CH₂Ph | Ph-4-F | 236–238 | A |
| 94 | Et | —CH₂Ph | Ph-4-OMe | 216–218 | A |
| 95 | Bu | Bu | Ph | 196–198 | A-IPE |
| 96 | Pr | Ph | Ph | 258–260 | A |

EXAMPLE 97

Preparation of 2-(4-chlorophenyl)-7,8-dihydro-8-oxo-N,N-dipropyl-9H-purin-9-acetamide A mixture of 2-[2-(4-chlorophenyl)-5-nitro-4-pyrimidinylamino]-N,N-dipropylacetamide (9 g), platinum (IV) oxide (1 g) and ethanol (150 ml) is stirred under hydrogen atmosphere for four hours, and the reaction mixture is filtered. The filtrate is concentrated under reduced pressure, and to the resulting residue is added urea (2.1 g). The mixture is stirred at 200° C. for two hours. After cooling, water is added to the reaction mixture, and the precipitates are collected by filtration, washed with water, and recrystallized from ethanol to give the desired compound (7 g).

M.p. 177–178° C.

EXAMPLES 98–105

The corresponding starting compounds are treated in the same manner as in Example 97 to give the compounds as listed in Table 20.

TABLE 20

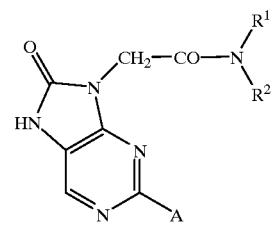

| Ex. | R¹ | R² | A | M.p. (° C.) | Solvent for recrystal. |
|---|---|---|---|---|---|
| 98 | Me | Ph | Ph | 286–287 | M |
| 99 | Me | Ph-3-Cl | Ph | 234–236 | M |
| 100 | Me | Ph-4-Cl | Ph | 244–246 | M |
| 101 | Me | Ph-4-OMe | Ph | 238–240 | A |
| 102 | Me | Ph-4-OMe | Ph-4-Cl | 277–280 | A |
| 103 | Et | Ph | Ph | 237–238 | A |
| 104 | Me | Me | Ph-4-CF₃ | >300 | A |
| 105 | Me | Me | Ph-3-CF₃ | 254–255 | A |

EXAMPLE 106

Preparation of 7,8-dihydro-7-methyl-8-oxo-2-phenyl-N,N-dipropyl-9H-purin-9-acetamide To a mixture of about 60% sodium hydride (oily) (0.8 g) and dimethylformamide (50 ml) is added 7,8-dihydro-8-oxo-2-phenyl-N,N-dipropyl-9H-purin-9-acetamide (6 g) obtained in Example 79 in portions at 0–5° C., and the mixture is stirred at 0° C. for one hour. To the mixture is added dropwise methyl iodide (2.9 g) at the same temperature. After the addition, the mixture is stirred at room temperature for two hours. To the reaction mixture are added water and chloroform, and the chloroform layer is separated, dried over anhydrous sodium sulfate, and concentrated under reduced pressure. The residue is purified by silica gel column chromatography (eluent; chloroform), and recrystallized from ethanol to give the desired compound (6 g).

M.p. 156–157° C.

EXAMPLES 107–172

The corresponding starting compounds are treated in the same manner as in Example 106 to give the compounds as listed in Table 21.

TABLE 21

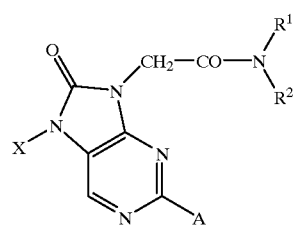

| Ex. | R¹ | R² | X | A | M.p. (° C.) | Solvent for recrystal. |
|---|---|---|---|---|---|---|
| 107 | Pr | Pr | Et | Ph | 98–99 | E |
| 108 | Pr | Pr | —CH₂Ph | Ph | 130–131 | IP |

TABLE 21-continued

Structure: Purine core with CH₂-CO-N(R¹)(R²) at N7, X at N9, A at C2, with 8-oxo group.

| Ex. | R¹ | R² | X | A | M.p. (° C.) | Solvent for re-crystal. |
|---|---|---|---|---|---|---|
| 109* | Pr | Pr | —CONH₂ | Ph | 183–185 | M |
| 110 | Pr | Pr | —CON(Me)₂ | Ph | 128–130 | E |
| 111 | Pr | Pr | Me | Ph-3-Cl | 166–167 | A |
| 112 | Pr | Pr | Me | Ph-4-Cl | 135–137 | IP |
| 113 | Pr | Pr | Me | Ph-4-F | 140–141 | A |
| 114 | Pr | Pr | Me | Ph-4-OMe | 157–158 | A |
| 115 | Pr | Pr | Me | Ph-4-NO₂ | 218–219 | A |
| 116 | Pr | Pr | Et | Ph-4-Cl | 158–159 | IP |
| 117 | Pr | Pr | Et | Ph-4-F | 134–136 | A |
| 118 | Pr | Pr | Et | Ph-4-OMe | 122–123 | A |
| 119 | Pr | Pr | Et | Ph-4-NO₂ | 179–180 | A |
| 120 | Pr | Pr | Pr | Ph | 125–127 | A-IPE |
| 121 | Pr | Pr | Pr | Ph-4-Cl | 107–108 | IP |
| 122 | Pr | Pr | Bu | Ph | 129–130 | A-IPE |
| 123 | Pr | Pr | Pent | Ph | 117–118 | A-IPE |
| 124 | Et | Et | Me | Ph | 204–206 | A |
| 125 | Et | Et | Et | Ph | 198–200 | A |
| 126 | Et | Et | Pr | Ph | 141–143 | A-IPE |
| 127 | Me | Me | Me | Ph | 262–264 | A-CF |
| 128 | Me | Me | Et | Ph | 187–189 | A |
| 129 | Me | Me | Me | Ph-4-CF₃ | 256–258 | A |
| 130 | Me | Me | Et | Ph-4-CF₃ | 230–232 | A |
| 131 | Me | Me | —CONH₂ | Ph-4-CF₃ | >300 | M |
| 132 | Me | Me | Me | Ph-3-CF₃ | 209–210 | A |
| 133 | Me | Me | Et | Ph-3-CF₃ | 173–174 | IP |
| 134 | Bu | Bu | Me | Ph | 192–193 | A |
| 135 | Bu | Bu | Et | Ph | 135–136 | A-IPE |
| 136 | Me | —CH₂Ph | Me | Ph | 169–170 | A-IPE |
| 137 | Me | —CH₂Ph | Me | Ph-4-Cl | 241–242 | A-CF |
| 138 | Me | —CH₂Ph | Me | Ph-4-F | 192–193 | A |
| 139 | Me | —CH₂Ph | Me | Ph-4-OMe | 197–199 | A |
| 140 | Me | —CH₂Ph | Et | Ph | 147–149 | A-IPE |
| 141 | Me | —CH₂Ph | Et | Ph-4-Cl | 197–198 | A |
| 142 | Me | —CH₂Ph | Et | Ph-4-F | 174–175 | A |
| 143 | Me | —CH₂Ph | Et | Ph-4-OMe | 161–162 | A |
| 144 | Me | —CH₂Ph | Pr | Ph | 155–157 | A |
| 145 | Me | —CH₂Ph | —CON(Me)₂ | Ph | 195–196 | A |
| 146 | Et | —CH₂Ph | Me | Ph | 163–164 | A |
| 147 | Et | —CH₂Ph | Me | Ph-4-Cl | 172–173 | A |
| 148 | Et | —CH₂Ph | Me | Ph-4-F | 169–170 | A |
| 149 | Et | —CH₂Ph | Me | Ph-4-OMe | 157–158 | A |
| 150 | Et | —CH₂Ph | Et | Ph | 134–136 | A-IPE |
| 151 | Et | —CH₂Ph | Et | Ph-4-Cl | 157–158 | A |
| 152 | Et | —CH₂Ph | Et | Ph-4-F | 135–136 | A-IPE |
| 153 | Et | —CH₂Ph | Et | Ph-4-OMe | 129–131 | IPE |
| 154 | Et | —CH₂Ph | Pr | Ph | 126–127 | A-IPE |
| 155 | Et | —CH₂Ph | —CON(Me)₂ | Ph | 152–153 | A-IPE |
| 156* | Me | Ph | Me | Ph | 202–203 | A |
| 157* | Me | Ph | Et | Ph | 170–171 | A |
| 158 | Me | Ph | Pr | Ph | 183–185 | A |
| 159 | Me | Ph | —CH₂Ph | Ph | 194–195 | A |
| 160 | Me | Ph | —CON(Me)₂ | Ph | 204–205 | A |
| 161 | Me | Ph-3-Cl | Et | Ph | 205–207 | A |
| 162 | Me | Ph-4-Cl | Et | Ph | 173–175 | A |
| 163 | Me | Ph-4-OMe | Me | Ph | 172–174 | IP |
| 164 | Me | Ph-4-OMe | Et | Ph | 142–144 | IP |
| 165 | Me | Ph-4-OMe | Et | Ph-4-Cl | 184–186 | IP |
| 166 | Et | Ph | Me | Ph | 180–181 | IP |
| 167 | Et | Ph | Et | Ph | 154–155 | A |
| 168 | Et | Ph | Pr | Ph | 140–142 | A |
| 169 | Pr | Ph | Me | Ph | 174–176 | A |
| 170 | Pr | Ph | Et | Ph | 151–152 | A |
| 171 | Me | Ph | Me | 3-Pyridyl | 216–217 | AN |
| 172 | Me | Ph | Et | 3-Pyridyl | 199–200 | AN |

*¼ hydrate

EXAMPLE 173

Preparation of 8,9-dihydro-N-(4-methoxyphenyl)-9-methyl-N-ethyl-8-oxo-2-phenyl-7H-purin-7-acetamide The corresponding starting compounds are treated in the same manner as in Example 48, and the resulting product is recrystallized from ethanol to give the desired compound.

M.p. 208–209° C.

EXAMPLE 174

Preparation of 8,9-dihydro-N-(4-hydroxyphenyl)-9-methyl-N-ethyl-8-oxo-2-phenyl-7H-purin-7-acetamide To a mixture of 8,9-dihydro-N-(4-methoxyphenyl)-methyl-N-ethyl-8-oxo-2-phenyl-7H-purin-7-acetamide (0.83 g) obtained in Example 173 and dichloromethane (10 ml) is added a 1M solution of boron tribromide in dichloromethane (4 ml) at 0° C., and the mixture is stirred at room temperature for five days. To the reaction mixture is added water, and the precipitates are collected by filtration, washed with water, and recrystallized from ethanol and diisopropyl ether to give the desired compound (0.38 g).

M.p. 254–256° C.

EXAMPLE 175

Preparation of N-benzyl-N-ethyl-7,8-dihydro-7-methyl-8-oxo-2-phenyl-9H-purin-9-acetamide hydrochloride To a mixture of N-benzyl-N-ethyl-7,8-dihydro-7-methyl-8-oxo-2-phenyl-9H-purin-9-acetamide (0.8 g) obtained in Example 146 and ethanol (15 ml) is added 30% hydrochloric acid in ethanol (15 ml) at 80° C., and the mixture is stirred for 30 minutes. The reaction mixture is cooled to room temperature, and the precipitates are collected by filtration, and washed with ethanol to give the desired compound (0.85 g).

M.p. 169–172° C.

EXAMPLE 176

Preparation of N-ethyl-8,9-dihydro-9-methyl-8-oxo-2-phenyl-N-phenyl-7H-purin-7-acetamide hydrochloride Using N-ethyl-8,9-dihydro-9-methyl-8-oxo-2-phenyl-N-phenyl-7H-purin-7-acetamide obtained in Example 1, the same procedures as Example 175 are repeated to give the desired compound.

M.p. 248–249° C.

EXAMPLES 177–186

The corresponding starting compounds are treated in the same manner as in Example 79 to give the compounds as listed in Table 22.

TABLE 22

| Ex. | R¹ | R² | A | M.p. (° C.) | Solvent for recrystal. |
|---|---|---|---|---|---|
| 177 | Me | Bzl-4-F | Ph | 269–270 | A |
| 178 | Me | Bzl-3-F | Ph | 256–258 | A |
| 179 | Me | Bzl-2-F | Ph | 234–235 | A-IPE |
| 180 | Me | Bzl-4-Cl | Ph | 276–277 | A-CF |
| 181 | Me | Bzl-4-OMe | Ph | 245–246 | A-IPE |
| 182 | Et | Bzl-4-F | Ph | 256–258 | A-CF |
| 183 | Et | Bzl-3-F | Ph | 217–219 | A-IPE |
| 184 | Et | Bzl-2-F | Ph | 200–203 | A-IPE |
| 185 | Et | Bzl-4-Cl | Ph | 234–236 | A-CF |
| 186 | Et | Bzl-4-OMe | Ph | 177–178 | A-IPE |

EXAMPLES 187–206

The corresponding starting compounds are treated in the same manner as in Example 106 to give the compounds as listed in Table 23.

TABLE 23

| Ex. | R¹ | R² | X | A | M.p. (° C.) | Solvent for recrystal. |
|---|---|---|---|---|---|---|
| 187 | Me | Bzl-4-F | Me | Ph | 207–208 | A |
| 188 | Me | Bzl-4-F | Et | Ph | 195–196 | A-IPE |
| 189 | Me | Bzl-3-F | Me | Ph | 173–175 | A |
| 190 | Me | Bzl-3-F | Et | Ph | 146–147 | A-IPE |
| 191 | Me | Bzl-2-F | Me | Ph | 164–166 | A-IPE |
| 192 | Me | Bzl-2-F | Et | Ph | 159–161 | A-IPE |
| 193 | Me | Bzl-4-Cl | Me | Ph | 244–245 | A-CF |
| 194 | Me | Bzl-4-Cl | Et | Ph | 203–205 | A |
| 195 | Me | Bzl-4-OMe | Me | Ph | 205–207 | A |
| 196 | Me | Bzl-4-OMe | Et | Ph | 183–185 | A-IPE |
| 197 | Et | Bzl-4-F | Me | Ph | 205–206 | A |
| 198 | Et | Bzl-4-F | Et | Ph | 155–156 | A-IPE |
| 199 | Et | Bzl-3-F | Me | Ph | 173–174 | A-IPE |
| 200 | Et | Bzl-3-F | Et | Ph | 147–148 | A-IPE |
| 201 | Et | Bzl-2-F | Me | Ph | 180–181 | A |
| 202 | Et | Bzl-2-F | Et | Ph | 159–160 | A-IPE |

TABLE 23-continued

| Ex. | R¹ | R² | X | A | M.p. (° C.) | Solvent for recrystal. |
|---|---|---|---|---|---|---|
| 203 | Et | Bzl-4-Cl | Me | Ph | 216–217 | A |
| 204 | Et | Bzl-4-Cl | Et | Ph | 141–142 | A-IPE |
| 205 | Et | Bzl-4-OMe | Me | Ph | 173–175 | A |
| 206 | Et | Bzl-4-OMe | Et | Ph | 153–154 | A |

The intermediates represented by the formula (II) are exemplified as follows.

EXAMPLE 207

Preparation of 7,9-dihydro-9-methyl-2-phenyl-8H-purin-8-one

To a mixture of 4-methylamino-2-phenylpyrimidine-5-carboxylic acid (7 g) and dimethylformamide (50 ml) is added triethylamine (3.1 g) at room temperature, and the mixture is stirred for 10 minutes, and thereto is added diphenylphosphoryl azide (8.4 g) at the same temperature. The reaction mixture is stirred at 120° C. for four hours, and concentrated under reduced pressure. The residue is poured into ice-water, and the precipitates are collected by filtration, washed with water, washed with ethanol, and recrystallized from chloroform to give the desired compound (5 g).

M.p. 286–289° C.

EXAMPLES 208–220

The corresponding starting compounds are treated in the same manner as in Example 207 to give the compounds as listed in Table 24.

TABLE 24

| Ex. | W | A | M.p. (° C.) | Solvent for recrystal. |
|---|---|---|---|---|
| 208 | H | Ph-3-Cl | 296–298 | CF |
| 209 | H | Ph-4-Cl | >300 | CF |
| 210 | H | Ph-4-F | >300 | CF |
| 211 | H | Ph-4-OMe | >300 | CF |
| 212 | H | Ph-4-NO₂ | >300 | CF |
| 213 | H | Ph-4-Me | 283–285 | CF |
| 214 | H | 3-Pyridyl | 293–294 | DMF |
| 215 | H | 2-Thienyl | >300 | CF |
| 216 | H | 3-Thienyl | 287–288 | CF |
| 217 | Ph | Ph | >300 | CF |
| 218 | Ph-4-CF₃ | Ph | >300 | M |

TABLE 24-continued

[Structure: purine-8-one core with N-CH3, HN, W at position, N, A position]

| Ex. | W | A | M.p. (° C.) | Solvent for recrystal. |
|---|---|---|---|---|
| 219 | Me | Ph-4-CF$_3$ | >300 | M |
| 220 | Ph | Ph-4-CF$_3$ | >300 | M |

EXAMPLE 221

Preparation of 7,9-dihydro-9-benzyl-2-phenyl-8H-purin-8-one

The corresponding starting compounds are treated in the same manner as in Example. 207 to give the desired compound.

M.p. 286–287° C. (recrystallized from chloroform).

EXAMPLE 222

Preparation of 7,9-dihydro-2-phenyl-9-propyl-8H-purin-8-one

The corresponding starting compounds are treated in the same manner as in Example 207 to give the desired compound.

M.p. 263–264° C. (recrystallized from ethanol).

EXAMPLE 223

Preparation of 9-ethyl-7,9-dihydro-2-phenyl-8H-purin-8-one

A mixture of 4-ethylamino-5-nitro-2-phenylpyrimidine (2.7 g), palladium-carbon (0.3 g), and ethanol (50 ml) is stirred at room temperature under hydrogen atmosphere for five hours, and the reaction mixture is filtered. The filtrate is concentrated under reduced pressure, and to the resulting residue is added urea (1.4 g). The mixture is stirred at 200° C. for two hours. After cooling, water is added to the reaction mixture, and the precipitates are collected by filtration, washed with water, and washed with ethanol to give the desired compound (2.4 g).

M.p. 268–270° C. (recrystallized from chloroform).

EXAMPLE 224

Preparation of 7,9-dihydro-9-methyl-2-(4-trifluoromethylphenyl)-8H-purin-8-one

The corresponding starting compounds are treated in the same manner as in Example 223, and the product is further recrystallized from isopropanol to give the desired compound.

M.p. 248–250° C.

EXAMPLE 225

Preparation of 6-chloro-7,9-dihydro-9-methyl-2-phenyl-8H-purin-8-one

The corresponding starting compounds are treated in the same manner as in Example 223 to give the desired compound as a solid.

Preparation 1: Preparation of Tablets

| | |
|---|---|
| N-Ethyl-8,9-dihydro-9-methyl-8-oxo-2-phenyl-N-phenyl-7H-purin-7-acetamide | 1 g |
| Lactose | 84 g |
| Corn starch | 30 g |
| Crystalline cellulose | 25 g |
| Hydroxypropyl cellulose | 3 g |

The above components are mixed and kneaded in a conventional manner, and the mixture is granulated. To the resultant are added light anhydrous silicic acid (0.7 g) and magnesium stearate (1.3 g), and the mixture is further tabletted to give 1,000 tablets (each 145 mg).

Preparation 2: Preparation of Capsules

| | |
|---|---|
| N-Ethyl-8,9-dihydro-9-methyl-8-oxo-2-phenyl-N-phenyl-7H-purin-7-acetamide | 2 g |
| Lactose | 165 g |
| Corn starch | 25 g |
| Hydroxypropyl cellulose | 3.5 g |
| Light anhydrous silicic acid | 1.8 g |
| Magnesium stearate | 2.7 g |

The above components are mixed and kneaded in a conventional manner, and the mixture is granulated, and each 200 mg of the resultant is packed into a capsule to give 1,000 capsules.

Preparation 3: Preparation of Powder

| | |
|---|---|
| N-Ethyl-8,9-dihydro-9-methyl-8-oxo-2-phenyl-N-phenyl-7H-purin-7-acetamide | 10 g |
| Lactose | 960 g |
| Hydroxypropyl cellulose | 25 g |
| Light anhydrous silicic acid | 5 g |

The above components are mixed by a conventional manner to give a powder preparation.

Industrial Applicability

As explained above, the present compounds of the formula (I) or a pharmaceutically acceptable acid addition salt thereof show a selective and remarkable affinity for the peripheral-type BZ$\omega_3$-receptor as well as show excellent pharmacological activities such as anti-anxiety activity, etc. in animal tests, and hence, they are useful in the prophylaxis or treatment of central nervous disorders such as anxiety-related diseases (neurosis, somatoform disorders, anxiety disorders, and others), depression, epilepsy, etc., or circulatory organs disorders such as angina pectoris, hypertension, etc. Besides, the compounds of the formula (II) of the present invention are useful as an intermediate for preparing the compound of the formula (I) wherein X is a group of the formula (Q).

What is claimed is:

1. A 2-aryl-8-oxodihydropurine derivative of the following formula

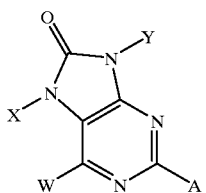
(I)

wherein:

W is a hydrogen atom, a lower alkyl group, a halogen atom, a lower alkoxy group, an amino group, a mono- or di-lower alkylamino group, or a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group;

X is a hydrogen atom, a lower alkyl group, a cycloalkyl-lower alkyl group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, a lower alkenyl group, a carbamoyl group, a di-lower alkylcarbamoyl group, or a group of the formula (Q):

(Q)

wherein:

$R^1$ is a lower alkyl group, lower alkenyl group, a cycloalkyl group, a cycloalkyl-lower alkyl group, or a hydroxyl-lower alkyl group, $R^2$ is a lower alkyl group, a cycloalkyl group, a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a 5-membered or 6-membered monocyclic heteroaryl group or a bicyclic heteroaryl group, each ring having 5 or 6 members, which heteroaryl group may optionally be substituted by a $C_1$–$C_3$ alkyl group or a trifluoromethyl group, and has at least one of a nitrogen atom, an oxygen atom and a sulfur atom, or $R^1$ and $R^2$ may combine together with the adjacent nitrogen atom to form a piperidine ring, a pyrrolidine ring, a morpholine ring or a piperazine ring, and these rings may optionally be substituted by one or two lower alkyl groups, and $R^3$ is a hydrogen atom, a lower alkyl group, or a hydroxy-lower alkyl group;

Y is a hydrogen atom, a lower alkyl group, a cycloalkyl group, a cycloalkyl-lower alkyl group, a lower alkenyl group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a group of the formula (Q):

(Q)

wherein $R^1$, $R^2$ and $R^3$ are the same as defined above; and

A is a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a 5-membered or 6-membered monocyclic heteroaryl group or a bicyclic heteroaryl group, each ring having 5 or 6 members, which heteroaryl group may optionally be substituted by a $C_1$–$C_3$ alkyl group or a trifluoromethyl group, and has at least one of a nitrogen atom, an oxygen atom and a sulfur atom;

provided that one of X and Y of the above formula(I) is the group of the formula (Q), and the other is not the group of the formula (Q), or a pharmaceutically acceptable acid addition salt thereof.

2. The compound according to claim 1, wherein A is a group of the formula (A'):

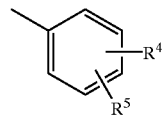
[A']

wherein $R^4$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group, and $R^5$ is a hydrogen atom, a halogen atom, a lower alkyl group, a lower alkoxy group, or a hydroxy group, a pyridyl group, a thienyl group or a furyl group.

3. The compound according to claim 1, wherein (a) X is a group of the formula (Qx):

(Qx)

wherein $R^{11}$ is a lower alkyl group, and $R^{21}$ is a lower alkyl group or a group of the formula (A"):

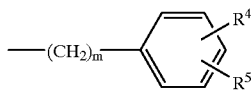
(A″)

wherein $R^4$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group, $R^5$ is a hydrogen atom, a halogen atom, a lower alkyl group, a lower alkoxy group, or a hydroxy group, and m is 0, 1 or 2, or $R^{11}$ and $R^{21}$ may combine together with the adjacent nitrogen atom to form a piperidine ring, a pyrrolidine ring, a morpholine ring, or a piperazine ring, and these rings may optionally be substituted by one or two lower alkyl groups, and $R^{31}$ is a hydrogen atom, a lower alkyl group, or a hydroxy-lower alkyl group, Y is a hydrogen atom or a lower alkyl group, or (b) X is a hydrogen atom, a lower alkyl group, or a carbamoyl group, Y is a group of the formula (Qy):

(Qy)

wherein $R^{11}$, $R^{21}$, and $R^{31}$ are the same as defined above.

4. The compound according to claim 3, wherein (a) X is the group of the above formula (Qx) wherein $R^{11}$ is a methyl group, an ethyl group, a propyl group, an isopropyl group, or a butyl group, $R^{21}$ is an ethyl group, a propyl group, an isopropyl group, a butyl group, a phenyl group, or a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is a hydrogen atom, a lower alkyl group, or a hydroxy-lower alkyl group, and Y is a hydrogen atom, a methyl group, or an ethyl group, or (b) X is a hydrogen atom, a methyl group, an ethyl group, a propyl group, an isopropyl group, or a butyl group, and Y is the group of the above formula (Qy) wherein $R^{11}$ is a methyl group, an ethyl group, a propyl group, an isopropyl group, or a butyl group, $R^{21}$ is an ethyl group, a propyl group, an isopropyl group, a butyl group, a phenyl group, a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is a hydrogen atom, a lower alkyl group, or a hydroxy-lower alkyl group.

5. The compound according to claim 2, wherein (a) X is a group of the formula (Qx):

(Qx)

wherein $R^{11}$ is a lower alkyl group, and $R^{21}$ is a lower alkyl group or a group of the formula (A″):

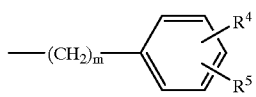
[A″]

wherein $R^4$ is a hydrogen atom, a halogen atom, a lower alkyl group, a lower alkoxy group, a trifluoromethyl group, a hydroxy group, an amino group, a mono- or di-lower alkylamino group, a cyano group, or a nitro group, $R^5$ is a hydrogen atom, a halogen atom, a lower alkyl group, a lower alkoxy group, or a hydroxy group, and m is 0, 1 or 2, or $R^{11}$ and $R^{21}$ may combine together with the adjacent nitrogen atom to form a piperidine ring, a pyrrolidine ring, a morpholine ring, or a piperazine ring, and these rings may optionally be substituted by one or two lower alkyl groups, and $R^{31}$ is a hydrogen atom, a lower alkyl group, or a hydroxy-lower alkyl group, Y is a hydrogen atom or a lower alkyl group, or (b) X is a hydrogen atom, a lower alkyl group, or a carbamoyl group, Y is a group of the formula (Qy):

(Qy)

wherein $R^{11}$, $R^{21}$, and $R^{31}$ are the same as defined above.

6. The compound according to claim 5, wherein (a) X is the group of the above formula (Qx) wherein $R^{11}$ is a methyl group, an ethyl group, a propyl group, an isopropyl group, or a butyl group, $R^{21}$ is an ethyl group, a propyl group, an isopropyl group, a butyl group, a phenyl group, or a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is a hydrogen atom, a lower alkyl group, or a hydroxy-lower alkyl group, and Y is a hydrogen atom, a methyl group, or an ethyl group, or (b) X is a hydrogen atom, a methyl group, an ethyl group, a propyl group, an isopropyl group, or a butyl group, and Y is the group of the above formula (Qy) wherein $R^{11}$ is a methyl group, an ethyl group, a propyl group, an isopropyl group, or a butyl group, $R^{21}$ is an ethyl group, a propyl group, an isopropyl group, a butyl group, a phenyl group, a phenyl group being substituted by a halogen, a methoxy, a trifluoromethyl, or a hydroxy, a benzyl group, or a benzyl group being substituted by a halogen, a methoxy, a trifluoromethyl, or a hydroxy, and $R^{31}$ is a hydrogen atom, a lower alkyl group, or a hydroxy-lower alkyl group.

7. A 2-aryl-8-oxodihydropurine derivative of the formula (Ia):

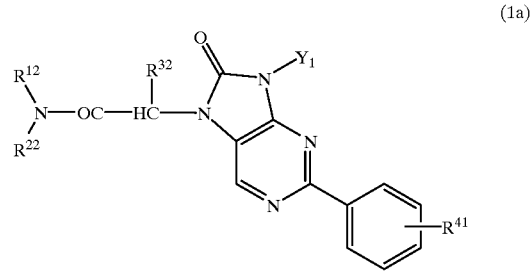
(Ia)

wherein $R^{12}$ and $R^{22}$ are the same or different, and each an ethyl group, a propyl group, or a butyl group, or $R^{12}$ is a methyl group, an ethyl group, or a propyl group, $R^{22}$ is a phenyl group, a halogenophenyl group, a methoxyphenyl group, a benzyl group, a halogenobenzyl group, or a methoxybenzyl group, $R^{32}$ is a hydrogen atom, a methyl group, or an ethyl group, $Y^1$ is a hydrogen atom, a methyl group, or an ethyl group, and $R^{41}$ is a hydrogen atom, a halogen atom, a methyl group, a methoxy group, a nitro group, or a trifluoromethyl group, or a pharmaceutically acceptable acid addition salt thereof.

8. The compound according to claim 7, wherein $R^{32}$ is a hydrogen atom.

9. A 2-aryl-8-oxodihydropurine derivative of the formula (Ib):

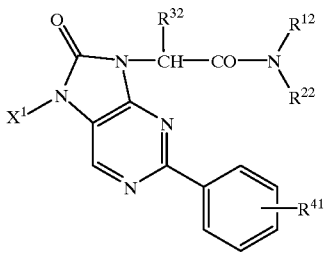

(Ib)

wherein $X^1$ is a hydrogen atom, a methyl group, an ethyl group, or a propyl group, $R^{12}$ and $R^{22}$ are the same or different, and each an ethyl group, a propyl group, or a butyl group, or $R^{12}$ is a methyl group, an ethyl group, or a propyl group, and $R^{22}$ is a phenyl group, a halogenophenyl group, a methoxyphenyl group, a benzyl group, a halogenobenzyl group, or a methoxybenzyl group, $R^{32}$ is a hydrogen atom, a methyl group, or an ethyl group, and $R^{41}$ is a hydrogen atom, a halogen atom, a methyl group, a methoxy group, a nitro group, or a trifluoromethyl group, or a pharmaceutically acceptable acid addition salt thereof.

10. The compound according to claim 9, wherein $R^{32}$ is a hydrogen atom.

11. A compound that is selected from the following compounds:

8,9-dihydro-9-methyl-N-methyl-8-oxo-2-phenyl-N-phenyl-7H-purine-7-acetamide;
8,9-dihydro-2-(4-fluorophenyl)-9-methyl-N-methyl-8-oxo-N-phenyl-7H-purine-7-acetamide;
N-ethyl-8,9-dihydro-2-(4-fluorophenyl)-9-methyl-8-oxo-N-phenyl-7H-purine-7-acetamide;
7,8-dihydro-7-methyl-8-oxo-2-phenyl-N,N-dipropyl-9H-purine-9-acetamide;
7-ethyl-7,8-dihydro-8-oxo-2-phenyl-N,N-dipropyl-9H-purine-9-acetamide;
N-ethyl-8,9-dihydro-9-methyl-8-oxo-2-phenyl-N-phenyl-7H-purine-7-acetamide;
N-benzyl-7,8-dihydro-N-methyl-7-methyl-8-oxo-2-phenyl-9H-purine-9-acetamide;
N-benzyl-N-ethyl-7,8-dihydro-7-methyl-8-oxo-2-(4-chlorophenyl)-9H-purine-9-acetamide; and
N-benzyl-7,8-dihydro-N-methyl-7-methyl-8-oxo-2-(4-chlorophenyl)-9H-purine-9-acetamide, or a pharmaceutically acceptable acid addition salt thereof.

12. N-Benzyl-N-ethyl-7,8-dihydro-7-methyl-8-oxo-2-phenyl-9H-purine-9-acetamide, or a pharmaceutically acceptable acid addition salt thereof.

13. A process for preparing a 2-aryl-8-oxodihydropurine derivative of the formula (I):

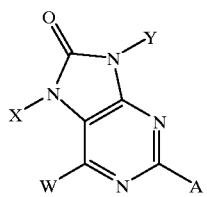

(I)

wherein:

W is a hydrogen atom, a lower alkyl group, a halogen atom, a lower alkoxy group, an amino group, a mono- or di-lower alkylamino group, or a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group;

X is a hydrogen atom, a lower alkyl group, a cycloalkyl-lower alkyl group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, a lower alkenyl group, a carbamoyl group, a di-lower alkylcarbamoyl group, or a group of the formula (Q):

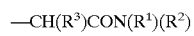—CH(R$^3$)CON(R$^1$)(R$^2$) (Q)

wherein:

$R^1$ is a lower alkyl group, lower alkenyl group, a cycloalkyl group, a cycloalkyl-lower alkyl group, or a hydroxyl-lower alkyl group, $R^2$ is a lower alkyl group, a cycloalkyl group, a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and nitro group, or a 5-membered or 6-membered monocyclic heteroaryl group or a bicyclic heteroaryl group, each ring having 5 or 6 members, which heteroaryl group may optionally be substituted by a $C_1$–$C_3$ alkyl group or a trifluoromethyl group, and has at least one of a nitrogen atom, an oxygen atom and a sulfur atom, or $R^1$ and $R^2$ may combine together with the adjacent nitrogen atom to form a piperidine ring, a pyrrolidine ring, a morpholine ring or a piperazine ring, and these rings may optionally be substituted by one or two lower alkyl groups, and $R^3$ is a hydrogen atom, a lower alkyl group, or a hydroxy-lower alkyl group;

Y is a hydrogen atom, a lower alkyl group, a cycloalkyl group, a cycloalkyl-lower alkyl group, a lower alkenyl group, an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a group of the formula (Q):

—CH($R^3$)CON($R^1$)($R^2$)  (Q)

wherein $R^1$, $R^2$ and $R^3$ are the same as defined above; and

A is a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a 5-membered or 6-membered monocyclic heteroaryl group or a bicyclic heteroaryl group, each ring having 5 or 6 members, which heteroaryl group may optionally be substituted by a $C_1$–$C_3$ alkyl group or a trifluoromethyl group, and has at least one of a nitrogen atom, an oxygen atom and a sulfur atom;

provided that one of X and Y of the above formula (I) is the group of the formula (Q), and the other is not a group of the formula (Q), or a pharmaceutically acceptable acid addition salt thereof, which comprises the following process (a), (b), (c), (d), or (e):

(a): when the compound (I) is a compound of the formula (I) wherein Y is a hydrogen atom, a lower alkyl group, a cycloalkyl group, a cycloalkyl-lower alkyl group, a lower alkenyl group, or an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, reacting a compound of the formula (II):

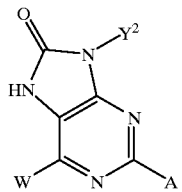

(II)

wherein:
$Y^2$ is a hydrogen atom, a lower alkyl group, a cycloalkyl group, a cycloalkyl-lower alkyl group, a lower alkenyl group, or an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, and
A and W are the same as defined above,
with a compound of the formula (III):

Z—CH($R^3$)—CON($R^1$)($R^2$)  (III)

wherein Z is a leaving atom or a leaving group, and $R^1$, $R^2$ and $R^3$ are the same as defined above;

(b): when the compound (I) is a compound of the formula (I) wherein X is a hydrogen atom, and Y is a group of the formula (Q), reacting a compound of the formula (IV):

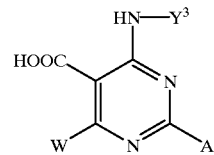

(IV)

wherein $Y^3$ is a group of the above formula (Q), and A and W are the same as defined above,
with an azide compound;

(c): when the compound (I) is a compound of the formula (1) wherein X is a hydrogen atom, and Y is a group of the formula (Q), reacting a compound of the formula (V):

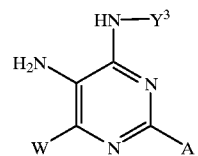

(V)

wherein A, W and $Y^3$ are the same as defined above,
with urea, a carbonyldiimidazole or a diethyl carbonate;

(d): when the compound (I) is a compound of the formula (I) wherein X is a group as defined above other than a hydrogen atom and other than a group of the formula (Q), and Y is a group of the formula (Q), reacting a compound of the formula (VI):

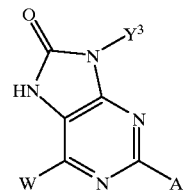

(VI)

wherein A, W and $Y^3$ are the same as defined above,
with a compound of the formula (VII):

Z—$X^2$  (VII)

wherein $X^2$ is a group which is the same as defined above for X other than a hydrogen atom and other than a group of the formula (Q), and Z is the same as defined above; and (e): when the compound (I) is a compound of the formula (I) wherein X is a group of the formula (Q), reacting a compound of the formula (VIII):

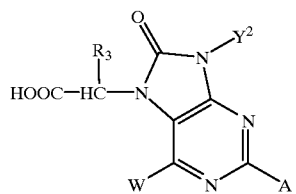

(VIII)

wherein A, $R^3$, W and $Y^2$ are the same as defined above, or a reactive derivative thereof,
with a compound of the formula (IX):

$HN(R^{13})(R^{23})$ (IX)

wherein $R^{13}$ and $R^{23}$ are each a hydrogen atom or the same groups for $R^1$ and $R^2$ as defined above, respectively, and when one of $R^{13}$ and $R^{23}$ is a hydrogen atom, then
further reacting the product with a compound of the formula (X):

$R^{24}$—Z (X)

or the formula (XI):

$R^{14}$—Z (XI)

wherein:
$R^{24}$ is a lower alkyl group, a cycloalkyl group, or an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group,
$R^{14}$ is a lower alkyl group, a lower alkenyl group, a cycloalkyl group, a cycloalkyl-lower alkyl group, or a hydroxyl-lower alkyl group, and
Z is the same as defined above,
provided that when $R^{13}$ is a hydrogen atom, then reacting with the compound (X), and when $R^{23}$ is a hydrogen atom, then reacting with the compound (XI) and if necessary, converting the product thus obtained into a pharmaceutically acceptable acid addition salt thereof.

14. A pharmaceutical composition, which comprises the 2-aryl-8-oxodihydropurine derivative as set forth in claim 1, or a pharmaceutically acceptable acid addition salt thereof, together with a pharmaceutically acceptable carrier or diluent.

15. A method for treatment of a neurosis, which comprises administering an effective amount of the 2-aryl-8-oxodihydropurine derivative as set forth in claim 1, or a pharmaceutically acceptable acid addition salt thereof, to a patient with said disease.

16. A 2-aryl-8-oxodihydropurine derivative of the formula (II):

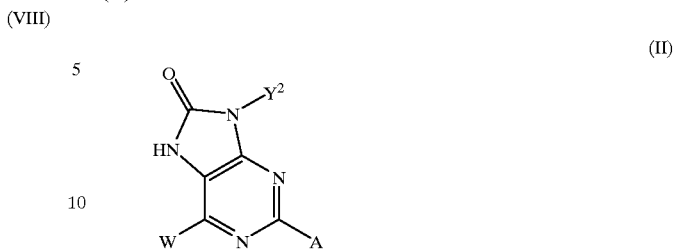

(II)

wherein:
W is a hydrogen atom, a lower alkyl group, a halogen atom, a lower alkoxy group, a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group,
$Y^2$ is a hydrogen atom, a lower alkyl group, a cycloalkyl group, a cycloalkyl-lower alkyl group, a lower alkenyl group, or an alkyl group having 1 to 4 carbon atoms which is substituted by a phenyl group being optionally substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, and
A is a phenyl group which may optionally be substituted by one or two groups selected from the group consisting of a halogen atom, a lower alkyl group, a lower alkoxy group, a trifluoromethyl group, a hydroxyl group, an amino group, a mono- or di-lower alkylamino group, a cyano group and a nitro group, or a 5-membered or 6-membered monocyclic heteroaryl group or a bicyclic heteroaryl group, each ring having 5 or 6 members, which heteroaryl group may optionally be substituted by a $C_1$–$C_3$ alkyl group or a trifluoromethyl group, and has at least one of a nitrogen atom, an oxygen atom and a sulfur atom.

17. A method for treatment of a somatoform disorder, which comprises administering an effective amount of the 2-aryl-8-oxodihydropurine derivative as set forth in claim 1, or a pharmaceutically acceptable acid addition salt thereof, to a patient with said disease.

18. A method for treatment of an anxiety disorder, which comprises administering an effective amount of the 2-aryl-8-oxodihydropurine derivative as set forth in claim 1, or a pharmaceutically acceptable acid addition salt thereof, to a patient with said disease.

* * * * *